US012781229B2

(12) United States Patent
Ogawa et al.

(10) Patent No.: US 12,781,229 B2
(45) Date of Patent: Nov. 3, 2026

(54) NUCLEIC ACID THAT INTERACTS WITH A RECEPTOR FOR ENDOCRINE DISRUPTING CHEMICALS AND USE THEREOF

(71) Applicants: KUMIAI CHEMICAL INDUSTRY CO., LTD., Tokyo (JP); UNIVERSITY PUBLIC CORPORATION OSAKA, Osaka (JP)

(72) Inventors: Masahiro Ogawa, Tokyo (JP); Sayoko Harashima, Sakai (JP); Masanobu Kawanishi, Sakai (JP); Takashi Yagi, Sakai (JP)

(73) Assignees: KUMIAI CHEMICAL INDUSTRY CO., LTD., Tokyo (JP); UNIVERSITY PUBLIC CORPORATION OSAKA, Osaka (JP)

( * ) Notice: Subject to any disclaimer, the term of this patent is extended or adjusted under 35 U.S.C. 154(b) by 873 days.

(21) Appl. No.: 17/920,250

(22) PCT Filed: Apr. 20, 2021

(86) PCT No.: PCT/JP2021/016086

§ 371 (c)(1),
(2) Date: Oct. 20, 2022

(87) PCT Pub. No.: WO2021/215451

PCT Pub. Date: Oct. 28, 2021

(65) Prior Publication Data

US 2023/0250436 A1 Aug. 10, 2023

(30) Foreign Application Priority Data

Apr. 21, 2020 (JP) ................................ 2020-075196

(51) Int. Cl.
*C12N 15/113* (2010.01)
*C07K 14/435* (2006.01)
*C07K 14/72* (2006.01)
*C12N 15/81* (2006.01)

(52) U.S. Cl.
CPC .... *C12N 15/1138* (2013.01); *C07K 14/43509* (2013.01); *C07K 14/43563* (2013.01); *C07K 14/72* (2013.01); *C12N 15/81* (2013.01); *C12N 2330/00* (2013.01)

(58) Field of Classification Search
CPC ................ C12N 15/1138; C12N 15/81; C12N 2330/00; C12N 15/63; C07K 14/43509; C07K 14/43563; C07K 14/72; C12Q 1/6897
See application file for complete search history.

(56) References Cited

FOREIGN PATENT DOCUMENTS

| | | | |
|---|---|---|---|
| JP | 2002-272 | A | 1/2002 |
| JP | 2003-505019 | A | 2/2003 |
| JP | 5754681 | B2 | 7/2015 |
| KR | 10-2004-0028321 | A | 4/2004 |
| KR | 10-2012-0092820 | A | 8/2012 |
| WO | WO 01/02436 | A1 | 1/2001 |

OTHER PUBLICATIONS

Gorr et al., "A candidate juvenoid hormone receptor cis-element in the *Daphnia magna* hb2 hemoglobin gene promoter," Molecular and Cellular Endocrinology, vol. 247, 2006, pp. 91-102.
Harashima et al., "Novel yeast reporter gene assay for detecting ligands of *Daphnia magna* juvenile hormone receptor via upstream E-box and E-box-like elements of the *Vrille* gene," Programs and Abstracts of 49th Annual Meeting of the Japanese Environmental Mutagen Society, 06-4, Nov. 13, 2020, p. 89 (total 2 pages).
He et al., "Heat Shock Protein 83 (Hsp83) Facilitates Methoprene-tolerant (Met) Nuclear Import to Modulate Juvenile Hormone Signaling," The Journal of Biological Chemistry, vol. 289, No. 40, 2014, pp. 27874-27885.
International Search Report (PCT/ISA/210) issued in PCT/JP2021/016086, dated Jul. 20, 2021.
Ishak et al., "Co-option of the bZIP transcription factor Vrille as the activator of *Doublesex1* in environmental sex determination of the crustacean *Daphnia magna*," PLOS Genetics, e1006953, 2017, pp. 1-19.
Ito-Harashima et al., "Establishment of reporter assay yeast strain for detecting ligands of *Daphnia magna* juvenile hormone receptor via upstream E-box and E-box-like elements of the *Vrille* gene," The Journal of Toxicological Sciences, vol. 45, Supplement, S 77-S 78, 0-5, Sep. 2020 (total 4 pages).
Tatarazako et al., "Juvenile hormone agonists affect the occurrence of male *Daphnia*," Chemosphere, vol. 53, 2003, pp. 827-833.
Toyota et al., "Methyl farnesoate synthesis is necessary for the environmental sex determination in the water flea *Daphnia pulex*," Journal of Insect Physiology, vol. 80, 2015, pp. 22-30.
Wang, et al., "The screening of chemicals for juvenoid-related endocrine activity using the water flea *Daphnia magna*," Aquatic Toxicology, vol. 74, 2005, pp. 193-204.
Written Opinion of the International Searching Authority (PCT/ISA/237) issued in PCT/JP2021/016086, dated Jul. 20, 2021.
Extended European Search Report for European Application No. 21792725.0, dated Apr. 26, 2024.
Ito-Harashima et al., "Reporter gene assays for screening and identification of novel molting hormone- and juvenile hormone-like chemicals," Journal of Pesticide Science, vol. 46, No. 1, 2021, pp. 29-42.
Harashima et al., "Detection of juvenile hormone receptor ligand substances via E-box/E-box-like sequences upstream of *Vrille* gene of Daphnia magna according to yeast reporter assay," Program and Abstracts, the Annual Meeting of the Molecular Biology Society of Japan, 1P-0347, 2020, p. 497.

(Continued)

*Primary Examiner* — J. E. Angell
(74) *Attorney, Agent, or Firm* — Birch, Stewart, Kolasch & Birch, LLP

(57) ABSTRACT

This invention provides a nucleic acid that enables evaluation of various endocrine disrupting actions of a very small amount of endocrine disrupting chemicals with high sensitivity. Such nucleic acid comprises a total of 20 to 60 nucleotides comprising the nucleotide sequence shown in SEQ ID NO: 1 and shows excellent responsiveness to various endocrine disrupting chemicals.

10 Claims, No Drawings

Specification includes a Sequence Listing.

(56) References Cited

OTHER PUBLICATIONS

"neuronal PAS domain-containing protein 2-like [Daphnia magna]," GenBank, URL:https://www.ncbi.nlm.nih.gov/protein/XP_032796650.1, Accession No. XP_032796650.1, Mar. 20, 2020, 2 pages.

Abe et al., "Diofenolan induces male offspring production through binding to the juvenile hormone receptor in Daphnia magna," Aquatic Toxicology, vol. 159, 2015, pp. 44-51.

Korean Office Action for Korean Application No. 10-2022-7039939, dated May 28, 2026, with English translation.

SEQUENCE LISTING

<160> NUMBER OF SEQ ID NOS: 54

<210> SEQ ID NO 1
<211> LENGTH: 16
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (7)..(10)
<223> OTHER INFORMATION: n is a, c, g, or t

<400> SEQUENCE: 1
cacgcgnnnn cacgtg 16

<210> SEQ ID NO 2
<211> LENGTH: 43
<212> TYPE: DNA
<213> ORGANISM: Daphnia magna

<400> SEQUENCE: 2
caaagaaaat acgcacacgc ggcggcacgt gtgtgcatcc cat 43

<210> SEQ ID NO 3
<211> LENGTH: 49
<212> TYPE: DNA
<213> ORGANISM: Artificial
<220> FEATURE:
<223> OTHER INFORMATION: Synthetic DNA

<400> SEQUENCE: 3
ctagtcaaag aaaatacgca cacgcggcgg cacgtgtgtg catcccatt 49

<210> SEQ ID NO 4
<211> LENGTH: 49
<212> TYPE: DNA
<213> ORGANISM: Artificial
<220> FEATURE:
<223> OTHER INFORMATION: Synthetic DNA

<400> SEQUENCE: 4
ctagaatggg atgcacacac gtgccgccgc gtgtgcgtat tttctttga 49

<210> SEQ ID NO 5

<211> LENGTH: 54
<212> TYPE: DNA
<213> ORGANISM: Daphnia magna

<400> SEQUENCE: 5
caaagaaaat acgcacacgc ggcggcacgt gtgtgcatcc catcttccgt tcgg 54

<210> SEQ ID NO 6
<211> LENGTH: 60
<212> TYPE: DNA
<213> ORGANISM: Artificial
<220> FEATURE:
<223> OTHER INFORMATION: Synthetic DNA

<400> SEQUENCE: 6
ctagtcaaag aaaatacgca cacgcggcgg cacgtgtgtg catcccatct tccgttcggt 60

<210> SEQ ID NO 7
<211> LENGTH: 60
<212> TYPE: DNA
<213> ORGANISM: Artificial
<220> FEATURE:
<223> OTHER INFORMATION: Synthetic DNA

<400> SEQUENCE: 7
ctagaccgaa cggaagatgg gatgcacaca cgtgccgccg cgtgtgcgta ttttctttga 60

<210> SEQ ID NO 8
<211> LENGTH: 30
<212> TYPE: DNA
<213> ORGANISM: Daphnia magna

<400> SEQUENCE: 8
atacgcacac gcggcggcac gtgtgtgcat 30

<210> SEQ ID NO 9
<211> LENGTH: 36
<212> TYPE: DNA
<213> ORGANISM: Artificial
<220> FEATURE:
<223> OTHER INFORMATION: Synthetic DNA

<400> SEQUENCE: 9
ctagtatacg cacacgcggc ggcacgtgtg tgcatt 36

<210> SEQ ID NO 10
<211> LENGTH: 36
<212> TYPE: DNA
<213> ORGANISM: Artificial
<220> FEATURE:
<223> OTHER INFORMATION: Synthetic DNA

<400> SEQUENCE: 10
ctagaatgca cacacgtgcc gccgcgtgtg cgtata 36

<210> SEQ ID NO 11
<211> LENGTH: 2088
<212> TYPE: DNA
<213> ORGANISM: Daphnia magna
<220> FEATURE:
<221> NAME/KEY: CDS
<222> LOCATION: (1)..(2088)

<400> SEQUENCE: 11 atg gac aaa atg agc gag aca tta cca agt tcg agc cgg gag atg cgg 48
Met Asp Lys Met Ser Glu Thr Leu Pro Ser Ser Ser Arg Glu Met Arg -continued

```
1               5                   10                  15

aat cgt gcg gag aag caa cgg cgt gac aag ctc aat gcc tac att tcg       96
Asn Arg Ala Glu Lys Gln Arg Arg Asp Lys Leu Asn Ala Tyr Ile Ser
            20                  25                  30

gag ctt tat agt ctc gtt ccg tca gcg gct gcc gcc cct agg aag ctg      144
Glu Leu Tyr Ser Leu Val Pro Ser Ala Ala Ala Ala Pro Arg Lys Leu
        35                  40                  45

gac aag acg agc acg ctc cgt ctt tcg gca aat ttt ttg cgc atc cat      192
Asp Lys Thr Ser Thr Leu Arg Leu Ser Ala Asn Phe Leu Arg Ile His
    50                  55                  60

caa aat atg gat cta cga atg aag ccg tac aac cga tgg aat gct tta      240
Gln Asn Met Asp Leu Arg Met Lys Pro Tyr Asn Arg Trp Asn Ala Leu
65                  70                  75                  80

gct ggt cat tca atc tta gag aaa ttg gac tcc ttt ttg ctt gtc gtc      288
Ala Gly His Ser Ile Leu Glu Lys Leu Asp Ser Phe Leu Leu Val Val
                85                  90                  95

tcg tgc tgc tct ggc aag atc atc tac gtc acg gat cga gtg gag aaa      336
Ser Cys Cys Ser Gly Lys Ile Ile Tyr Val Thr Asp Arg Val Glu Lys
            100                 105                 110

ttg ctc gga cat gcg cag gtc gat atg atg ggc tac cag tta tcc tgt      384
Leu Leu Gly His Ala Gln Val Asp Met Met Gly Tyr Gln Leu Ser Cys
        115                 120                 125

ttt gtc cac cag gca gat caa gat gca att gaa aaa cgg ctc agt gct      432
Phe Val His Gln Ala Asp Gln Asp Ala Ile Glu Lys Arg Leu Ser Ala
    130                 135                 140

ttt gct gca caa gtg gct gct aat cca gat gct tca gat tct gcc gat      480
Phe Ala Ala Gln Val Ala Ala Asn Pro Asp Ala Ser Asp Ser Ala Asp
145                 150                 155                 160

gga caa gtc tat tca ttc gaa tgt cgc cta gcc gga cgc caa ctc agt      528
Gly Gln Val Tyr Ser Phe Glu Cys Arg Leu Ala Gly Arg Gln Leu Ser
                165                 170                 175

cgg ggc gaa ccg acc gtc tat gaa cgg gtc agt gtc tca ggg act ttt      576
Arg Gly Glu Pro Thr Val Tyr Glu Arg Val Ser Val Ser Gly Thr Phe
            180                 185                 190

cga ggc cct cgg aga aga cgt gac tgg gct gat ctc aaa agc agt gat      624
Arg Gly Pro Arg Arg Arg Arg Asp Trp Ala Asp Leu Lys Ser Ser Asp
        195                 200                 205

aga tct gtg gca act gtt caa caa cac aac gac tac agc gag ccg ctt      672
Arg Ser Val Ala Thr Val Gln Gln His Asn Asp Tyr Ser Glu Pro Leu
    210                 215                 220

ttt att ggc ttg gtg cgc att tta caa aca ccc aac act tta cct cca      720
Phe Ile Gly Leu Val Arg Ile Leu Gln Thr Pro Asn Thr Leu Pro Pro
225                 230                 235                 240

ttg acg atc atg caa gct gtt cag gac gag tat atc act cag cac aca      768
Leu Thr Ile Met Gln Ala Val Gln Asp Glu Tyr Ile Thr Gln His Thr
                245                 250                 255

acc ggt ggc acc att ata caa acc gat cat cgc atc gcc atc att gct      816
Thr Gly Gly Thr Ile Ile Gln Thr Asp His Arg Ile Ala Ile Ile Ala
            260                 265                 270

ggt tat ctg agt ggc gag gtg acg ggc atg tca gca tac gat tat gtt      864
Gly Tyr Leu Ser Gly Glu Val Thr Gly Met Ser Ala Tyr Asp Tyr Val
        275                 280                 285

tat agc gaa gat ttg gag tac act ctc aaa gct caa agc ctc atg tta      912
Tyr Ser Glu Asp Leu Glu Tyr Thr Leu Lys Ala Gln Ser Leu Met Leu
    290                 295                 300

act cgg agt gaa gga atg gtg act tat cgc cta aaa acc agt acg ggt      960
Thr Arg Ser Glu Gly Met Val Thr Tyr Arg Leu Lys Thr Ser Thr Gly
305                 310                 315                 320

cgt ttg att ttc ctt cga tca aga ggt ttc atc caa tac gat gaa aac     1008
```

```
Arg Leu Ile Phe Leu Arg Ser Arg Gly Phe Ile Gln Tyr Asp Glu Asn
                325                 330                 335

acg aag gaa att gtc agc ttc ttc tgc atc aat tca ctc atc gac gaa      1056
Thr Lys Glu Ile Val Ser Phe Phe Cys Ile Asn Ser Leu Ile Asp Glu
            340                 345                 350

gag caa gga atg aag gaa atg cag gaa atg cgg gcc atg tta gac aaa      1104
Glu Gln Gly Met Lys Glu Met Gln Glu Met Arg Ala Met Leu Asp Lys
        355                 360                 365

ctt aac att gca act gtt acg cca gcg ata gcg tca tcg cca acg agc      1152
Leu Asn Ile Ala Thr Val Thr Pro Ala Ile Ala Ser Ser Pro Thr Ser
    370                 375                 380

acg att gaa cca gtt gga gca gct tct act caa gag cca ctt tct cgt      1200
Thr Ile Glu Pro Val Gly Ala Ala Ser Thr Gln Glu Pro Leu Ser Arg
385                 390                 395                 400

tgt gtt cgg gcg tca gtg ggg aaa cca ccg cct tct ttt tct tct aat      1248
Cys Val Arg Ala Ser Val Gly Lys Pro Pro Pro Ser Phe Ser Ser Asn
                405                 410                 415

ggc tgc cac ctt gcg aat ggg tct agg gtc tcg ggc ctg cct aga tcc      1296
Gly Cys His Leu Ala Asn Gly Ser Arg Val Ser Gly Leu Pro Arg Ser
            420                 425                 430

agt att atg ccc aac gga cat aac agt tta tgc att tca ccc tcc tct      1344
Ser Ile Met Pro Asn Gly His Asn Ser Leu Cys Ile Ser Pro Ser Ser
        435                 440                 445

gaa ctt cag tac tcc cct tca gga tcg tct tcg tct tct ttc agt gaa      1392
Glu Leu Gln Tyr Ser Pro Ser Gly Ser Ser Ser Ser Ser Phe Ser Glu
    450                 455                 460

gaa cgt tgc caa tct tct aca ccg cat tcg ctc gtg tca tct ccc atg      1440
Glu Arg Cys Gln Ser Ser Thr Pro His Ser Leu Val Ser Ser Pro Met
465                 470                 475                 480

gaa att cct aat tta gtt gct gtt tcc tac cca ttt gca ccc ata cct      1488
Glu Ile Pro Asn Leu Val Ala Val Ser Tyr Pro Phe Ala Pro Ile Pro
                485                 490                 495

ttc cca tgg cga cca tcg aca gac tgt tct ccg atc acc acg aca tct      1536
Phe Pro Trp Arg Pro Ser Thr Asp Cys Ser Pro Ile Thr Thr Thr Ser
            500                 505                 510

aac ggt cac gtt aac act aga gaa gtt agc aaa tcc ccc gat gtc gat      1584
Asn Gly His Val Asn Thr Arg Glu Val Ser Lys Ser Pro Asp Val Asp
        515                 520                 525

cag agc gat cct ctt ggt gaa cca gga ttg ctg gct ctt acg ctg gat      1632
Gln Ser Asp Pro Leu Gly Glu Pro Gly Leu Leu Ala Leu Thr Leu Asp
    530                 535                 540

cat caa tgg gaa acg gct ccc aat agt cag agc atg atc gtc cag cac      1680
His Gln Trp Glu Thr Ala Pro Asn Ser Gln Ser Met Ile Val Gln His
545                 550                 555                 560

aat ggg cca caa agt cat cag cag tcc ttg gta gcc gtc agt ccc ctt      1728
Asn Gly Pro Gln Ser His Gln Gln Ser Leu Val Ala Val Ser Pro Leu
                565                 570                 575

caa gct cat ttg ctt cag tca tcg cca aac gat aac ata gaa ccg att      1776
Gln Ala His Leu Leu Gln Ser Ser Pro Asn Asp Asn Ile Glu Pro Ile
            580                 585                 590

cgg tcc acc ctg aaa tcg ccg cca tcg tcc acc agc tgt ccc gtt caa      1824
Arg Ser Thr Leu Lys Ser Pro Pro Ser Ser Thr Ser Cys Pro Val Gln
        595                 600                 605

cct ccc cac caa tat cag gaa gat gct ctg aaa atc tcg att ccc gat      1872
Pro Pro His Gln Tyr Gln Glu Asp Ala Leu Lys Ile Ser Ile Pro Asp
    610                 615                 620

cgt tgt ccg acg aat gaa ctg agt cga aac aac tgt ctc aac ggc tac      1920
Arg Cys Pro Thr Asn Glu Leu Ser Arg Asn Asn Cys Leu Asn Gly Tyr
625                 630                 635                 640
```

```
atc att tgg cct caa aag atg tcg ccc aaa aat cga aag gag aat ctt      1968
Ile Ile Trp Pro Gln Lys Met Ser Pro Lys Asn Arg Lys Glu Asn Leu
                645                 650                 655

ata ttg tcg tac ttg gac gtc gac aag cat gcc tac aaa cag cca gag      2016
Ile Leu Ser Tyr Leu Asp Val Asp Lys His Ala Tyr Lys Gln Pro Glu
            660                 665                 670

att acc gga act gct gac cag cac tac tat cat agt gat tta aaa gtg      2064
Ile Thr Gly Thr Ala Asp Gln His Tyr Tyr His Ser Asp Leu Lys Val
        675                 680                 685

aat gct gga acc aac agt gca tag                                      2088
Asn Ala Gly Thr Asn Ser Ala
    690                 695


<210> SEQ ID NO 12
<211> LENGTH: 695
<212> TYPE: PRT
<213> ORGANISM: Daphnia magna

<400> SEQUENCE: 12

Met Asp Lys Met Ser Glu Thr Leu Pro Ser Ser Ser Arg Glu Met Arg
1               5                   10                  15

Asn Arg Ala Glu Lys Gln Arg Arg Asp Lys Leu Asn Ala Tyr Ile Ser
            20                  25                  30

Glu Leu Tyr Ser Leu Val Pro Ser Ala Ala Ala Ala Pro Arg Lys Leu
        35                  40                  45

Asp Lys Thr Ser Thr Leu Arg Leu Ser Ala Asn Phe Leu Arg Ile His
    50                  55                  60

Gln Asn Met Asp Leu Arg Met Lys Pro Tyr Asn Arg Trp Asn Ala Leu
65                  70                  75                  80

Ala Gly His Ser Ile Leu Glu Lys Leu Asp Ser Phe Leu Leu Val Val
                85                  90                  95

Ser Cys Cys Ser Gly Lys Ile Ile Tyr Val Thr Asp Arg Val Glu Lys
            100                 105                 110

Leu Leu Gly His Ala Gln Val Asp Met Met Gly Tyr Gln Leu Ser Cys
        115                 120                 125

Phe Val His Gln Ala Asp Gln Asp Ala Ile Glu Lys Arg Leu Ser Ala
    130                 135                 140

Phe Ala Ala Gln Val Ala Ala Asn Pro Asp Ala Ser Asp Ser Ala Asp
145                 150                 155                 160

Gly Gln Val Tyr Ser Phe Glu Cys Arg Leu Ala Gly Arg Gln Leu Ser
                165                 170                 175

Arg Gly Glu Pro Thr Val Tyr Glu Arg Val Ser Val Ser Gly Thr Phe
            180                 185                 190

Arg Gly Pro Arg Arg Arg Arg Asp Trp Ala Asp Leu Lys Ser Ser Asp
        195                 200                 205

Arg Ser Val Ala Thr Val Gln Gln His Asn Asp Tyr Ser Glu Pro Leu
    210                 215                 220

Phe Ile Gly Leu Val Arg Ile Leu Gln Thr Pro Asn Thr Leu Pro Pro
225                 230                 235                 240

Leu Thr Ile Met Gln Ala Val Gln Asp Glu Tyr Ile Thr Gln His Thr
                245                 250                 255

Thr Gly Gly Thr Ile Ile Gln Thr Asp His Arg Ile Ala Ile Ile Ala
            260                 265                 270

Gly Tyr Leu Ser Gly Glu Val Thr Gly Met Ser Ala Tyr Asp Tyr Val
        275                 280                 285

Tyr Ser Glu Asp Leu Glu Tyr Thr Leu Lys Ala Gln Ser Leu Met Leu
```

-continued

```
    290                 295                 300

Thr Arg Ser Glu Gly Met Val Thr Tyr Arg Leu Lys Thr Ser Thr Gly
305                 310                 315                 320

Arg Leu Ile Phe Leu Arg Ser Arg Gly Phe Ile Gln Tyr Asp Glu Asn
                325                 330                 335

Thr Lys Glu Ile Val Ser Phe Phe Cys Ile Asn Ser Leu Ile Asp Glu
            340                 345                 350

Glu Gln Gly Met Lys Glu Met Gln Glu Met Arg Ala Met Leu Asp Lys
        355                 360                 365

Leu Asn Ile Ala Thr Val Thr Pro Ala Ile Ala Ser Ser Pro Thr Ser
    370                 375                 380

Thr Ile Glu Pro Val Gly Ala Ala Ser Thr Gln Glu Pro Leu Ser Arg
385                 390                 395                 400

Cys Val Arg Ala Ser Val Gly Lys Pro Pro Pro Ser Phe Ser Ser Asn
                405                 410                 415

Gly Cys His Leu Ala Asn Gly Ser Arg Val Ser Gly Leu Pro Arg Ser
            420                 425                 430

Ser Ile Met Pro Asn Gly His Asn Ser Leu Cys Ile Ser Pro Ser Ser
        435                 440                 445

Glu Leu Gln Tyr Ser Pro Ser Gly Ser Ser Ser Ser Ser Phe Ser Glu
    450                 455                 460

Glu Arg Cys Gln Ser Ser Thr Pro His Ser Leu Val Ser Ser Pro Met
465                 470                 475                 480

Glu Ile Pro Asn Leu Val Ala Val Ser Tyr Pro Phe Ala Pro Ile Pro
                485                 490                 495

Phe Pro Trp Arg Pro Ser Thr Asp Cys Ser Pro Ile Thr Thr Thr Ser
            500                 505                 510

Asn Gly His Val Asn Thr Arg Glu Val Ser Lys Ser Pro Asp Val Asp
        515                 520                 525

Gln Ser Asp Pro Leu Gly Glu Pro Gly Leu Leu Ala Leu Thr Leu Asp
    530                 535                 540

His Gln Trp Glu Thr Ala Pro Asn Ser Gln Ser Met Ile Val Gln His
545                 550                 555                 560

Asn Gly Pro Gln Ser His Gln Gln Ser Leu Val Ala Val Ser Pro Leu
                565                 570                 575

Gln Ala His Leu Leu Gln Ser Ser Pro Asn Asp Asn Ile Glu Pro Ile
            580                 585                 590

Arg Ser Thr Leu Lys Ser Pro Pro Ser Ser Thr Ser Cys Pro Val Gln
        595                 600                 605

Pro Pro His Gln Tyr Gln Glu Asp Ala Leu Lys Ile Ser Ile Pro Asp
    610                 615                 620

Arg Cys Pro Thr Asn Glu Leu Ser Arg Asn Asn Cys Leu Asn Gly Tyr
625                 630                 635                 640

Ile Ile Trp Pro Gln Lys Met Ser Pro Lys Asn Arg Lys Glu Asn Leu
                645                 650                 655

Ile Leu Ser Tyr Leu Asp Val Asp Lys His Ala Tyr Lys Gln Pro Glu
            660                 665                 670

Ile Thr Gly Thr Ala Asp Gln His Tyr Tyr His Ser Asp Leu Lys Val
        675                 680                 685

Asn Ala Gly Thr Asn Ser Ala
    690                 695

<210> SEQ ID NO 13
```

```
<211> LENGTH: 6672
<212> TYPE: DNA
<213> ORGANISM: Daphnia magna
<220> FEATURE:
<221> NAME/KEY: CDS
<222> LOCATION: (1)..(6672)

<400> SEQUENCE: 13

atg ctg acg gat acc gca ttc ctg gat gat gca cag agt ttg ggt gca       48
Met Leu Thr Asp Thr Ala Phe Leu Asp Asp Ala Gln Ser Leu Gly Ala
1               5                   10                  15

att cca tgc gag tca cta tcg tcc gag ccg tgc tgg gcc aac atg aat       96
Ile Pro Cys Glu Ser Leu Ser Ser Glu Pro Cys Trp Ala Asn Met Asn
            20                  25                  30

acg ctc agc agc ggc ggc gga ggt ggt ggc ggc agc ggt ggt agc agc      144
Thr Leu Ser Ser Gly Gly Gly Gly Gly Gly Gly Ser Gly Gly Ser Ser
        35                  40                  45

aat agc aac agc cca ggt ctc ggc agc aac aac aac aat cat acg acg      192
Asn Ser Asn Ser Pro Gly Leu Gly Ser Asn Asn Asn Asn His Thr Thr
    50                  55                  60

tcg tcg gcc tca ccg acg acg acg acg acg acc ggc aac agc aac agc      240
Ser Ser Ala Ser Pro Thr Thr Thr Thr Thr Thr Gly Asn Ser Asn Ser
65                  70                  75                  80

agc ggc ggt ggc gct ggc ggc agc aac ggc ctc acc ggc acc tcg gcg      288
Ser Gly Gly Gly Ala Gly Gly Ser Asn Gly Leu Thr Gly Thr Ser Ala
                85                  90                  95

gcc gcc atc aaa aag cga cgc aaa tcc gac acg aag ccg ctg tcg caa      336
Ala Ala Ile Lys Lys Arg Arg Lys Ser Asp Thr Lys Pro Leu Ser Gln
            100                 105                 110

atc aac aag tgt ctc aac gaa aaa aga cgt cgc gaa cag gaa aac gtc      384
Ile Asn Lys Cys Leu Asn Glu Lys Arg Arg Arg Glu Gln Glu Asn Val
        115                 120                 125

tac att gaa gag ttg gct gaa ttg att tcg gtg agc att gcc gac gtg      432
Tyr Ile Glu Glu Leu Ala Glu Leu Ile Ser Val Ser Ile Ala Asp Val
    130                 135                 140

aac tcg ctg tct gtg aaa ccg gac aag tgc gcc att tta caa gag acg      480
Asn Ser Leu Ser Val Lys Pro Asp Lys Cys Ala Ile Leu Gln Glu Thr
145                 150                 155                 160

gtc aat cag atc cga aag atc cgt gaa cag gaa gaa gac gga cga agt      528
Val Asn Gln Ile Arg Lys Ile Arg Glu Gln Glu Glu Asp Gly Arg Ser
                165                 170                 175

tcg agt agc agt agt agc agc agc agc agc acc agt tcg aat ggt agt      576
Ser Ser Ser Ser Ser Ser Ser Ser Ser Ser Thr Ser Ser Asn Gly Ser
            180                 185                 190

agc acc aac agt tct ggc acg agt tca gcc aat agc gga aca gga gga      624
Ser Thr Asn Ser Ser Gly Thr Ser Ser Ala Asn Ser Gly Thr Gly Gly
        195                 200                 205

acc gta gga gct gta ggg gca gga gga gca gga gga gcc gta gga gcc      672
Thr Val Gly Ala Val Gly Ala Gly Gly Ala Gly Gly Ala Val Gly Ala
    210                 215                 220

gta gga gcc gta gga gga ggt gga cag ggc aac aac acg acg tcg ccc      720
Val Gly Ala Val Gly Gly Gly Gly Gln Gly Asn Asn Thr Thr Ser Pro
225                 230                 235                 240

ggc gga gtg act gat ggc ggc gtc ggg ccg ctg ctc caa cag ggc gac      768
Gly Gly Val Thr Asp Gly Gly Val Gly Pro Leu Leu Gln Gln Gly Asp
                245                 250                 255

gtt tca tca tcg aaa ccg gcc ctg cta gac acg caa ctt ttg ggt acg      816
Val Ser Ser Ser Lys Pro Ala Leu Leu Asp Thr Gln Leu Leu Gly Thr
            260                 265                 270

ttc ctg ctc gaa gcc ctt gac ggc ttc ctg ttt gtc gtc aac acg gaa      864
Phe Leu Leu Glu Ala Leu Asp Gly Phe Leu Phe Val Val Asn Thr Glu
```

-continued

```
        275                 280                 285

ggg aaa acg gag tat gtc tct gaa aat gtc gcc cat ttt cta cac tac      912
Gly Lys Thr Glu Tyr Val Ser Glu Asn Val Ala His Phe Leu His Tyr
    290                 295                 300

caa ccg caa gat ctc gtc ggc aaa tcc atc tac aat ttt atc cac cac      960
Gln Pro Gln Asp Leu Val Gly Lys Ser Ile Tyr Asn Phe Ile His His
305                 310                 315                 320

gga gat cac gcc cgt ttt tcg tcg tcg ctc tta ccc acg gcc atc gcg     1008
Gly Asp His Ala Arg Phe Ser Ser Ser Leu Leu Pro Thr Ala Ile Ala
                325                 330                 335

tgg ccg agt gaa atg gca cca acg tct cag aac agg ata ggt cgc tgt     1056
Trp Pro Ser Glu Met Ala Pro Thr Ser Gln Asn Arg Ile Gly Arg Cys
            340                 345                 350

ttc aat tgc cga tta ctg atc cag ccg ctt ggc gag caa gac gaa acg     1104
Phe Asn Cys Arg Leu Leu Ile Gln Pro Leu Gly Glu Gln Asp Glu Thr
        355                 360                 365

atg gag gag aag cag cag cga gtc gaa cac tat gag aac atg caa ata     1152
Met Glu Glu Lys Gln Gln Arg Val Glu His Tyr Glu Asn Met Gln Ile
    370                 375                 380

tct gcc gtt ctc cag ccg tat cca gcg gac ggt ggc cag cag cag cag     1200
Ser Ala Val Leu Gln Pro Tyr Pro Ala Asp Gly Gly Gln Gln Gln Gln
385                 390                 395                 400

cag cca aca aag aaa atc agc ggg gca gcg gca gct gcg gcc gca gcc     1248
Gln Pro Thr Lys Lys Ile Ser Gly Ala Ala Ala Ala Ala Ala Ala Ala
                405                 410                 415

gca gcc gcc gtc ggc ttg gag acg tcc gat ttg gaa ctg gcg ctg acg     1296
Ala Ala Ala Val Gly Leu Glu Thr Ser Asp Leu Glu Leu Ala Leu Thr
            420                 425                 430

tct gtg gct agc ggc tcg ctc gca ggt gat ccg cag cac tgc ctc gtg     1344
Ser Val Ala Ser Gly Ser Leu Ala Gly Asp Pro Gln His Cys Leu Val
        435                 440                 445

tgc gta gcc agg cgc att ccg tcg acg gag aaa atg gct gcc gcc aac     1392
Cys Val Ala Arg Arg Ile Pro Ser Thr Glu Lys Met Ala Ala Ala Asn
    450                 455                 460

ccg acg gtt gga ggt cca atc gtg gaa cag ttc acc acc aaa ttg gac     1440
Pro Thr Val Gly Gly Pro Ile Val Glu Gln Phe Thr Thr Lys Leu Asp
465                 470                 475                 480

ccg agt ggc aag ata gta gcc gtc gat gtg acg ggc gtt tct tcg ccc     1488
Pro Ser Gly Lys Ile Val Ala Val Asp Val Thr Gly Val Ser Ser Pro
                485                 490                 495

tac agt tcc tac ttg agc aaa gag gcg ctc gtc tcg tgt acg atc cag     1536
Tyr Ser Ser Tyr Leu Ser Lys Glu Ala Leu Val Ser Cys Thr Ile Gln
            500                 505                 510

gag ctc tgc tac ccc gac gat ttg ccc gtt ttc cag gcg cat cta cag     1584
Glu Leu Cys Tyr Pro Asp Asp Leu Pro Val Phe Gln Ala His Leu Gln
        515                 520                 525

gaa acg ctg cat tcc ggc tgc ggc atc agc tcc aga tat cgg ctc aga     1632
Glu Thr Leu His Ser Gly Cys Gly Ile Ser Ser Arg Tyr Arg Leu Arg
    530                 535                 540

ttg acc ggc gcc tcc acc ccg atg ggt cac cgt ggt ggc gcc ggc gga     1680
Leu Thr Gly Ala Ser Thr Pro Met Gly His Arg Gly Gly Ala Gly Gly
545                 550                 555                 560

ggc agc gga ggc ttt ctc gtc gtt caa acc aag tcg aaa cgt ttc att     1728
Gly Ser Gly Gly Phe Leu Val Val Gln Thr Lys Ser Lys Arg Phe Ile
                565                 570                 575

cac ggt gac acg cac gag acg gac ttt atc atg gcc acg cat tcc atc     1776
His Gly Asp Thr His Glu Thr Asp Phe Ile Met Ala Thr His Ser Ile
            580                 585                 590

atc gtc gat gac gac ggt gaa gat gtc gac act ggc aac agc agc agc     1824
```

```
Ile Val Asp Asp Asp Gly Glu Asp Val Asp Thr Gly Asn Ser Ser Ser
        595                 600                 605

agc aac acc aac acc aac acc agc cga atg atg ttg ttg gcg gcc gcg      1872
Ser Asn Thr Asn Thr Asn Thr Ser Arg Met Met Leu Leu Ala Ala Ala
    610                 615                 620

agc gac acg ctc aac gac cat cac cgt cta tcg gaa tcg acg ggc agt      1920
Ser Asp Thr Leu Asn Asp His His Arg Leu Ser Glu Ser Thr Gly Ser
625                 630                 635                 640

atc atc agt cag ccg cag caa cag cag caa cag cag cag cag cag cag      1968
Ile Ile Ser Gln Pro Gln Gln Gln Gln Gln Gln Gln Gln Gln Gln Gln
                645                 650                 655

cag cag cag cag agc aac ccg gtg ctc acc agc gtc gtc cgc cac gat      2016
Gln Gln Gln Gln Ser Asn Pro Val Leu Thr Ser Val Val Arg His Asp
            660                 665                 670

gtg ata tca gcc acc agt ttc ggc aac agc ggc tgc agt ggt ggc gcc      2064
Val Ile Ser Ala Thr Ser Phe Gly Asn Ser Gly Cys Ser Gly Gly Ala
        675                 680                 685

acg acg gca acc act tcc tcc acc tcc tcc tcc tcc tac tcc agt acc      2112
Thr Thr Ala Thr Thr Ser Ser Thr Ser Ser Ser Ser Tyr Ser Ser Thr
    690                 695                 700

ttc gcc gga ctc agt ctg gga acg agc ggc gat ctt ctc aat gac ttt      2160
Phe Ala Gly Leu Ser Leu Gly Thr Ser Gly Asp Leu Leu Asn Asp Phe
705                 710                 715                 720

gtc gtg ccc gac ttg ttc atg gct tca ccg ccc tgg gat ttc aat aac      2208
Val Val Pro Asp Leu Phe Met Ala Ser Pro Pro Trp Asp Phe Asn Asn
                725                 730                 735

agc gag tcg agc ctg gac gac ggc ggc agc ggc gtc gcg ctg gcc gcc      2256
Ser Glu Ser Ser Leu Asp Asp Gly Gly Ser Gly Val Ala Leu Ala Ala
            740                 745                 750

gcc tcg gct gcc gct tcg gcc gct gtt gcc gcc gct gct caa atc acc      2304
Ala Ser Ala Ala Ala Ser Ala Ala Val Ala Ala Ala Ala Gln Ile Thr
        755                 760                 765

aac agt cac cac ttg cag gcc gtc acg gcc acg tcc agc ctg cag ctc      2352
Asn Ser His His Leu Gln Ala Val Thr Ala Thr Ser Ser Leu Gln Leu
    770                 775                 780

tcg gtt ccg tcg cct ctc tcc ctc atc ccg tcg ggc ggt cct ctc ttg      2400
Ser Val Pro Ser Pro Leu Ser Leu Ile Pro Ser Gly Gly Pro Leu Leu
785                 790                 795                 800

gcc ggc cac cta ccc cat cat tct gtt ggc gga atg atc aac tgg ggc      2448
Ala Gly His Leu Pro His His Ser Val Gly Gly Met Ile Asn Trp Gly
                805                 810                 815

agc cct ccg ccg tcg gcc ggt gcc ggg gga gta gga caa cga gcc ggc      2496
Ser Pro Pro Pro Ser Ala Gly Ala Gly Gly Val Gly Gln Arg Ala Gly
            820                 825                 830

tcg aca ccg tgc gga caa atg gcg acc gtc atg ggc tcg tcg agg ccc      2544
Ser Thr Pro Cys Gly Gln Met Ala Thr Val Met Gly Ser Ser Arg Pro
        835                 840                 845

agc tcg aga caa agc gcc tcg tcg aca ccg cga ccg ccc agc gtg tct      2592
Ser Ser Arg Gln Ser Ala Ser Ser Thr Pro Arg Pro Pro Ser Val Ser
    850                 855                 860

tca gcc ttc agt ccg gct ccc aat tcc gtc ctg ggc gtc gtt cat ccg      2640
Ser Ala Phe Ser Pro Ala Pro Asn Ser Val Leu Gly Val Val His Pro
865                 870                 875                 880

tca ccc gtg ctc agt cca gtc ggc gcc acc agc atc cat tca gcc gca      2688
Ser Pro Val Leu Ser Pro Val Gly Ala Thr Ser Ile His Ser Ala Ala
                885                 890                 895

atg tct tgc acc agc ggt ttg gtc act ggc tcc acg tcg tcg tca tcg      2736
Met Ser Cys Thr Ser Gly Leu Val Thr Gly Ser Thr Ser Ser Ser Ser
            900                 905                 910
```

-continued

```
gct ggc cag caa caa ccc agt ccg gcc agt atg acg aca ccc ttt agc     2784
Ala Gly Gln Gln Gln Pro Ser Pro Ala Ser Met Thr Thr Pro Phe Ser
        915                 920                 925

aac aat ttc ccg ttc agt cca ctc caa gat ccc att cct cag cat ccg     2832
Asn Asn Phe Pro Phe Ser Pro Leu Gln Asp Pro Ile Pro Gln His Pro
    930                 935                 940

gca acg gct ccg cag acc cat aat ccg gcc acc cct ttc ctg gac gaa     2880
Ala Thr Ala Pro Gln Thr His Asn Pro Ala Thr Pro Phe Leu Asp Glu
945                 950                 955                 960

gtc cgt gac acc aag gac gga atc atc tcg tcc ggc cct ggt ggt agt     2928
Val Arg Asp Thr Lys Asp Gly Ile Ile Ser Ser Gly Pro Gly Gly Ser
                965                 970                 975

gtt agc cac ggt cac aac tac ctg tct ggt gga tct cac cac cag cag     2976
Val Ser His Gly His Asn Tyr Leu Ser Gly Gly Ser His His Gln Gln
            980                 985                 990

cag cat cat cat cat cat caa caa  caa caa cag caa caa  caa cag caa    3024
Gln His His His His His Gln Gln  Gln Gln Gln Gln Gln  Gln Gln Gln
        995                 1000                1005

caa cac  gcg acc gac aaa caa  atg agc gct ctc agt  agt tta ttg      3069
Gln His  Ala Thr Asp Lys Gln  Met Ser Ala Leu Ser  Ser Leu Leu
    1010                 1015                 1020

aac tgt  aac gac gct gcc aca  tca tcg tcg tcg tct  tcg tcg tcc      3114
Asn Cys  Asn Asp Ala Ala Thr  Ser Ser Ser Ser Ser  Ser Ser Ser
    1025                 1030                 1035

tct tcg  tct tct tca tct tct  tcc tcg ttg gcc gaa  tct ggc cgg      3159
Ser Ser  Ser Ser Ser Ser Ser  Ser Ser Leu Ala Glu  Ser Gly Arg
    1040                 1045                 1050

tta cgc  att ttg ctc atg caa  aga ccg ggc aac gct  ccg cca ccc      3204
Leu Arg  Ile Leu Leu Met Gln  Arg Pro Gly Asn Ala  Pro Pro Pro
    1055                 1060                 1065

tca gcc  cat cag cag cca ggt  cat tct agc agt ggt  agt agt agt      3249
Ser Ala  His Gln Gln Pro Gly  His Ser Ser Ser Gly  Ser Ser Ser
    1070                 1075                 1080

agt agt  agt agt aca agt aca  agt aca agt aca agt  aca agt aca      3294
Ser Ser  Ser Ser Thr Ser Thr  Ser Thr Ser Thr Ser  Thr Ser Thr
    1085                 1090                 1095

agt aca  aat aca aat aca aat  act aat agt agc aac  aac aat aac      3339
Ser Thr  Asn Thr Asn Thr Asn  Thr Asn Ser Ser Asn  Asn Asn Asn
    1100                 1105                 1110

aac aac  aac aac aac gct agc  ggc aac aac aac agc  agt agt gtc      3384
Asn Asn  Asn Asn Asn Ala Ser  Gly Asn Asn Asn Ser  Ser Ser Val
    1115                 1120                 1125

aac ggg  agc cat ctg ttg gcg  gct ttg ggc gac gct  gag gcc gtc      3429
Asn Gly  Ser His Leu Leu Ala  Ala Leu Gly Asp Ala  Glu Ala Val
    1130                 1135                 1140

aaa cgc  gaa aaa gat gaa aat  agc ggt gcg ccc tct  tgt ggc tcg      3474
Lys Arg  Glu Lys Asp Glu Asn  Ser Gly Ala Pro Ser  Cys Gly Ser
    1145                 1150                 1155

ttg agc  gtc acc aaa ggc agt  cac ggc aac cgc att  ctc aaa ggg      3519
Leu Ser  Val Thr Lys Gly Ser  His Gly Asn Arg Ile  Leu Lys Gly
    1160                 1165                 1170

ttg ctg  aac cag gac gat ggc  gat gaa gct gat caa  gcg gac gat      3564
Leu Leu  Asn Gln Asp Asp Gly  Asp Glu Ala Asp Gln  Ala Asp Asp
    1175                 1180                 1185

acg agc  aat cat cgc ttc ttg  ttg acg gcc aga ggc  aac ctt tct      3609
Thr Ser  Asn His Arg Phe Leu  Leu Thr Ala Arg Gly  Asn Leu Ser
    1190                 1195                 1200

gga gac  gga gtc aag acc agt  agt agc gcg ggc aac  aac aac aac      3654
Gly Asp  Gly Val Lys Thr Ser  Ser Ser Ala Gly Asn  Asn Asn Asn
    1205                 1210                 1215
```

```
aac acc  acc aac acc aac aac  aat aac acc aac aac  aac aac aac      3699
Asn Thr  Thr Asn Thr Asn Asn  Asn Asn Thr Asn Asn  Asn Asn Asn
    1220                 1225                 1230

atg ctg  cac aaa ttg ttg aat  gtg cgg agc gac gac  gat gcc gag      3744
Met Leu  His Lys Leu Leu Asn  Val Arg Ser Asp Asp  Asp Ala Glu
    1235                 1240                 1245

cag cgg  atg ggt ctg cgc aag  ccc aac gaa ttg ctc  aag aaa ctt      3789
Gln Arg  Met Gly Leu Arg Lys  Pro Asn Glu Leu Leu  Lys Lys Leu
    1250                 1255                 1260

ctc aag  gac ccc gaa gag gat  cac caa cag gca agt  gga aac ggc      3834
Leu Lys  Asp Pro Glu Glu Asp  His Gln Gln Ala Ser  Gly Asn Gly
    1265                 1270                 1275

agc agc  agt gcc tgt ggc ggc  acc gga agc ggt ggc  acg gcc aac      3879
Ser Ser  Ser Ala Cys Gly Gly  Thr Gly Ser Gly Gly  Thr Ala Asn
    1280                 1285                 1290

cag ctc  caa caa ttt cac cac  caa cgt caa cag cag  cag cag caa      3924
Gln Leu  Gln Gln Phe His His  Gln Arg Gln Gln Gln  Gln Gln Gln
    1295                 1300                 1305

caa cag  caa cac cag caa cac  cag caa cac cag caa  cac caa caa      3969
Gln Gln  Gln His Gln Gln His  Gln Gln His Gln Gln  His Gln Gln
    1310                 1315                 1320

agt cag  cag caa cag caa cag  aat caa cat cat cat  tca gat cag      4014
Ser Gln  Gln Gln Gln Gln Gln  Asn Gln His His His  Ser Asp Gln
    1325                 1330                 1335

gtg tcg  ttc cag gaa gag caa  tta ctg aaa tcg ttt  ggt ttc cca      4059
Val Ser  Phe Gln Glu Glu Gln  Leu Leu Lys Ser Phe  Gly Phe Pro
    1340                 1345                 1350

tca ccg  aca gcc tcg tca ggt  tcg tct acg gca gca  acg gtt gca      4104
Ser Pro  Thr Ala Ser Ser Gly  Ser Ser Thr Ala Ala  Thr Val Ala
    1355                 1360                 1365

acg gga  tct ttg gcc aac atg  ttg gct acc agt caa  atg act cat      4149
Thr Gly  Ser Leu Ala Asn Met  Leu Ala Thr Ser Gln  Met Thr His
    1370                 1375                 1380

ctc aga  tct cct caa ccg cca  ggc atg tcg agc cat  tgc gac gga      4194
Leu Arg  Ser Pro Gln Pro Pro  Gly Met Ser Ser His  Cys Asp Gly
    1385                 1390                 1395

ttg ttg  gag ttt ggc gga gtt  gtt tgt agc agt acg  acc gcc agt      4239
Leu Leu  Glu Phe Gly Gly Val  Val Cys Ser Ser Thr  Thr Ala Ser
    1400                 1405                 1410

ggc atg  gtg ttt ggt ggc aat  gct gcc gtt ggt gga  gct agt ggg      4284
Gly Met  Val Phe Gly Gly Asn  Ala Ala Val Gly Gly  Ala Ser Gly
    1415                 1420                 1425

atg cgg  ggc acg aaa agg cac  agc gaa gaa gct cgt  gac gag gtg      4329
Met Arg  Gly Thr Lys Arg His  Ser Glu Glu Ala Arg  Asp Glu Val
    1430                 1435                 1440

aaa gcc  agc aaa gag ccc atg  ctg agc gcc gac cac  ctg atg atg      4374
Lys Ala  Ser Lys Glu Pro Met  Leu Ser Ala Asp His  Leu Met Met
    1445                 1450                 1455

tcc gca  ggc gga ggc ggg gtc  ttg cac cag ctg ttg  ggt cct ccg      4419
Ser Ala  Gly Gly Gly Gly Val  Leu His Gln Leu Leu  Gly Pro Pro
    1460                 1465                 1470

cca ctg  tcg acg gcg tcg acg  tca tcc tct tct tcc  gca tct tcc      4464
Pro Leu  Ser Thr Ala Ser Thr  Ser Ser Ser Ser Ser  Ala Ser Ser
    1475                 1480                 1485

tcg tct  gcc tgc tct tct tcg  gct gcg ttg tct tcg  tcg ttg gcg      4509
Ser Ser  Ala Cys Ser Ser Ser  Ala Ala Leu Ser Ser  Ser Leu Ala
    1490                 1495                 1500

cca tcg  aat gcg cac agt gtt  gca gcc acg act ctt  gcg ata gcc      4554
Pro Ser  Asn Ala His Ser Val  Ala Ala Thr Thr Leu  Ala Ile Ala
```

```
    1505                1510                1515

gcg ttg  caa cat caa cct ctt  tcg tcg cca tcg aca  gca gct gcc      4599
Ala Leu  Gln His Gln Pro Leu  Ser Ser Pro Ser Thr  Ala Ala Ala
    1520                1525                1530

gtc gcg  gcc gcc acg tcg gcc  gtg gct gcg gcc gca  gct acg gcc      4644
Val Ala  Ala Ala Thr Ser Ala  Val Ala Ala Ala Ala  Ala Thr Ala
    1535                1540                1545

aac gcg  atg gct tct caa ttg  caa gca gcg cct agt  gcc cag tca      4689
Asn Ala  Met Ala Ser Gln Leu  Gln Ala Ala Pro Ser  Ala Gln Ser
    1550                1555                1560

gcc gcc  gct gcc gtt gct gct  gcc gcc gcc gcc gcc  gcc gcc gcc      4734
Ala Ala  Ala Ala Val Ala Ala  Ala Ala Ala Ala Ala  Ala Ala Ala
    1565                1570                1575

gcc gct  gct gct gct gcc aat  ctg ccg gcc agc agt  aaa ttg tgc      4779
Ala Ala  Ala Ala Ala Ala Asn  Leu Pro Ala Ser Ser  Lys Leu Cys
    1580                1585                1590

gaa aaa  aat aag atg ttg gct  tcg tta ttg gcc aag  acg ccc gtg      4824
Glu Lys  Asn Lys Met Leu Ala  Ser Leu Leu Ala Lys  Thr Pro Val
    1595                1600                1605

atg ccg  tcg ccg tcg tcg acc  aat att gcc tcg ccc  aaa ccg tca      4869
Met Pro  Ser Pro Ser Ser Thr  Asn Ile Ala Ser Pro  Lys Pro Ser
    1610                1615                1620

gcg ttg  cct cag gag aaa ttg  cct aag gat ttg aag  gag aaa att      4914
Ala Leu  Pro Gln Glu Lys Leu  Pro Lys Asp Leu Lys  Glu Lys Ile
    1625                1630                1635

ctt cag  acg ccg cca gtc agt  gga acg tcg gct ccg  ggc gcc cat      4959
Leu Gln  Thr Pro Pro Val Ser  Gly Thr Ser Ala Pro  Gly Ala His
    1640                1645                1650

tgg gct  gga ggc tcg gtg caa  acc cag ccc ccg acg  act atg caa      5004
Trp Ala  Gly Gly Ser Val Gln  Thr Gln Pro Pro Thr  Thr Met Gln
    1655                1660                1665

ttg ccc  ccg cat ccg gcg atc  caa caa cct cag caa  cag caa caa      5049
Leu Pro  Pro His Pro Ala Ile  Gln Gln Pro Gln Gln  Gln Gln Gln
    1670                1675                1680

cac gtt  ctt aac cag caa caa  cag cag cag caa cag  cag cag cag      5094
His Val  Leu Asn Gln Gln Gln  Gln Gln Gln Gln Gln  Gln Gln Gln
    1685                1690                1695

cag cag  caa cag caa cag caa  cag caa cag caa cag  caa caa cag      5139
Gln Gln  Gln Gln Gln Gln Gln  Gln Gln Gln Gln Gln  Gln Gln Gln
    1700                1705                1710

caa cga  cat ccg gcc atg caa  caa tca cag cag cat  cag tta cac      5184
Gln Arg  His Pro Ala Met Gln  Gln Ser Gln Gln His  Gln Leu His
    1715                1720                1725

cct cga  tct cag cat ctt cca  caa caa cat cag cat  ttg aac ctc      5229
Pro Arg  Ser Gln His Leu Pro  Gln Gln His Gln His  Leu Asn Leu
    1730                1735                1740

ggt cag  aag caa cag cag caa  cca act cct caa acc  ggt gga ttc      5274
Gly Gln  Lys Gln Gln Gln Gln  Pro Thr Pro Gln Thr  Gly Gly Phe
    1745                1750                1755

ttg aat  tct ctc ctg aac cgg  ccc ata gat tcc gcc  tcg ggt ccc      5319
Leu Asn  Ser Leu Leu Asn Arg  Pro Ile Asp Ser Ala  Ser Gly Pro
    1760                1765                1770

aat att  atc gga gag tct caa  caa cag gcc aat cag  cag cag cag      5364
Asn Ile  Ile Gly Glu Ser Gln  Gln Gln Ala Asn Gln  Gln Gln Gln
    1775                1780                1785

cag cag  caa caa caa caa caa  caa caa cta tat tta  gct gct caa      5409
Gln Gln  Gln Gln Gln Gln Gln  Gln Gln Leu Tyr Leu  Ala Ala Gln
    1790                1795                1800

cag cct  ccg cct gtc caa ctt  cag cat cga ccc aat  cag acg gta      5454
```

```
Gln Pro  Pro Pro Val Gln Leu  Gln His Arg Pro Asn  Gln Thr Val
    1805                 1810                 1815

cag aaa  ttg tcg ctc aac aac  caa caa cag ctt tcg  gcg gct atg      5499
Gln Lys  Leu Ser Leu Asn Asn  Gln Gln Gln Leu Ser  Ala Ala Met
    1820                 1825                 1830

aac tcg  tct ggt ggt ttc aac  att tct ctt cat cct  caa caa cac      5544
Asn Ser  Ser Gly Gly Phe Asn  Ile Ser Leu His Pro  Gln Gln His
    1835                 1840                 1845

cag cag  cag cag cag cag cat  cat cac cac ctt caa  cag cag cag      5589
Gln Gln  Gln Gln Gln Gln His  His His His Leu Gln  Gln Gln Gln
    1850                 1855                 1860

cag caa  caa caa caa cac cat  cag cag cag cag cag  cag cag cag      5634
Gln Gln  Gln Gln Gln His His  Gln Gln Gln Gln Gln  Gln Gln Gln
    1865                 1870                 1875

caa caa  caa caa caa caa caa  caa caa caa caa cag  cat cat caa      5679
Gln Gln  Gln Gln Gln Gln Gln  Gln Gln Gln Gln Gln  His His Gln
    1880                 1885                 1890

ctg cag  cat caa ctc tct ggt  tct atg ctg gcc gat  cgt ggc ctt      5724
Leu Gln  His Gln Leu Ser Gly  Ser Met Leu Ala Asp  Arg Gly Leu
    1895                 1900                 1905

ttg caa  gct ggc gga gga ccg  ggc caa cga tcc ggc  atg tcg atc      5769
Leu Gln  Ala Gly Gly Gly Pro  Gly Gln Arg Ser Gly  Met Ser Ile
    1910                 1915                 1920

cag ccg  caa cag cag acg tcg  cat gcc aat tcc atg  att gca gcc      5814
Gln Pro  Gln Gln Gln Thr Ser  His Ala Asn Ser Met  Ile Ala Ala
    1925                 1930                 1935

gcc agt  ttg gaa agc agc gat  ggc agc tac agc gtt  cac gcc gac      5859
Ala Ser  Leu Glu Ser Ser Asp  Gly Ser Tyr Ser Val  His Ala Asp
    1940                 1945                 1950

ttt atg  act ccg ctg gac gtc  caa atg gct tct gtg  gcc ggc tgg      5904
Phe Met  Thr Pro Leu Asp Val  Gln Met Ala Ser Val  Ala Gly Trp
    1955                 1960                 1965

ggt gac  acg cct tcc atg gat  ccg gag ctt tcc gac  atc att gag      5949
Gly Asp  Thr Pro Ser Met Asp  Pro Glu Leu Ser Asp  Ile Ile Glu
    1970                 1975                 1980

cag gtc  atc gac atg gat gag  cgc tac gag agc gat  tcg atg att      5994
Gln Val  Ile Asp Met Asp Glu  Arg Tyr Glu Ser Asp  Ser Met Ile
    1985                 1990                 1995

ttc ggc  gaa ttg aca tcg gtc  acg cca ccg cca gtc  gcc atc cag      6039
Phe Gly  Glu Leu Thr Ser Val  Thr Pro Pro Pro Val  Ala Ile Gln
    2000                 2005                 2010

ccc gtc  ctg tcc gtt cag tcg  tcg caa gcg atc gct  tcg gtg gct      6084
Pro Val  Leu Ser Val Gln Ser  Ser Gln Ala Ile Ala  Ser Val Ala
    2015                 2020                 2025

caa gcg  act gcc att gtc ggc  cca cta ggc ccg cac  ctt caa atg      6129
Gln Ala  Thr Ala Ile Val Gly  Pro Leu Gly Pro His  Leu Gln Met
    2030                 2035                 2040

gac atg  tcg aaa gag aaa ctg  gcc atc acg gcc att  caa aag tcg      6174
Asp Met  Ser Lys Glu Lys Leu  Ala Ile Thr Ala Ile  Gln Lys Ser
    2045                 2050                 2055

ctc atg  tcc tac gag aag att  ccc acc gta gct caa  agt cct ccg      6219
Leu Met  Ser Tyr Glu Lys Ile  Pro Thr Val Ala Gln  Ser Pro Pro
    2060                 2065                 2070

gcc tac  aat ctg ccc ggc tac  gca caa cag ggt caa  gga gca ccg      6264
Ala Tyr  Asn Leu Pro Gly Tyr  Ala Gln Gln Gly Gln  Gly Ala Pro
    2075                 2080                 2085

acg aga  atg tcc act cca act  tac ggc atg aat tca  gca ccg gcc      6309
Thr Arg  Met Ser Thr Pro Thr  Tyr Gly Met Asn Ser  Ala Pro Ala
    2090                 2095                 2100
```

```
agt tca  ttg ccc atg gcg aat  caa caa ctg caa acc  aac ttg acg      6354
Ser Ser  Leu Pro Met Ala Asn  Gln Gln Leu Gln Thr  Asn Leu Thr
    2105                 2110                 2115

atg ccg  gga gct aga aaa cag  aaa tta ccc gtt cag  caa aga cga      6399
Met Pro  Gly Ala Arg Lys Gln  Lys Leu Pro Val Gln  Gln Arg Arg
    2120                 2125                 2130

ctg gct  aat aga caa cag caa  cag cag cag cag caa  cag cag cag      6444
Leu Ala  Asn Arg Gln Gln Gln  Gln Gln Gln Gln Gln  Gln Gln Gln
    2135                 2140                 2145

cag caa  cag cag cag caa cag  caa cag caa cag cag  cag cag cag      6489
Gln Gln  Gln Gln Gln Gln Gln  Gln Gln Gln Gln Gln  Gln Gln Gln
    2150                 2155                 2160

tca tcg  tcg caa gaa caa caa  caa caa caa caa caa  cca gct cct      6534
Ser Ser  Ser Gln Glu Gln Gln  Gln Gln Gln Gln Gln  Pro Ala Pro
    2165                 2170                 2175

cag cag  cag cta cta ggc gtc  ttg ctg aat gaa tcg  tct gta caa      6579
Gln Gln  Gln Leu Leu Gly Val  Leu Leu Asn Glu Ser  Ser Val Gln
    2180                 2185                 2190

cac acc  caa ggg gca cag ctc  tca ccc gga gcc ttg  caa att atg      6624
His Thr  Gln Gly Ala Gln Leu  Ser Pro Gly Ala Leu  Gln Ile Met
    2195                 2200                 2205

gat gac  cta ctt aac gcg atc  cca ccc aac atg acg  ata tcc agg      6669
Asp Asp  Leu Leu Asn Ala Ile  Pro Pro Asn Met Thr  Ile Ser Arg
    2210                 2215                 2220

taa                                                                 6672
```

<210> SEQ ID NO 14
<211> LENGTH: 2223
<212> TYPE: PRT
<213> ORGANISM: Daphnia magna

<400> SEQUENCE: 14

```
Met Leu Thr Asp Thr Ala Phe Leu Asp Asp Ala Gln Ser Leu Gly Ala
1               5                   10                  15

Ile Pro Cys Glu Ser Leu Ser Ser Glu Pro Cys Trp Ala Asn Met Asn
            20                  25                  30

Thr Leu Ser Ser Gly Gly Gly Gly Gly Gly Gly Ser Gly Gly Ser Ser
        35                  40                  45

Asn Ser Asn Ser Pro Gly Leu Gly Ser Asn Asn Asn Asn His Thr Thr
    50                  55                  60

Ser Ser Ala Ser Pro Thr Thr Thr Thr Thr Thr Gly Asn Ser Asn Ser
65                  70                  75                  80

Ser Gly Gly Gly Ala Gly Gly Ser Asn Gly Leu Thr Gly Thr Ser Ala
                85                  90                  95

Ala Ala Ile Lys Lys Arg Arg Lys Ser Asp Thr Lys Pro Leu Ser Gln
            100                 105                 110

Ile Asn Lys Cys Leu Asn Glu Lys Arg Arg Arg Glu Gln Glu Asn Val
        115                 120                 125

Tyr Ile Glu Glu Leu Ala Glu Leu Ile Ser Val Ser Ile Ala Asp Val
    130                 135                 140

Asn Ser Leu Ser Val Lys Pro Asp Lys Cys Ala Ile Leu Gln Glu Thr
145                 150                 155                 160

Val Asn Gln Ile Arg Lys Ile Arg Glu Gln Glu Glu Asp Gly Arg Ser
                165                 170                 175

Ser Ser Ser Ser Ser Ser Ser Ser Ser Ser Thr Ser Ser Asn Gly Ser
            180                 185                 190

Ser Thr Asn Ser Ser Gly Thr Ser Ser Ala Asn Ser Gly Thr Gly Gly
```

```
        195                 200                 205

Thr Val Gly Ala Val Gly Ala Gly Gly Ala Gly Gly Ala Val Gly Ala
    210                 215                 220

Val Gly Ala Val Gly Gly Gly Gly Gln Gly Asn Asn Thr Thr Ser Pro
225                 230                 235                 240

Gly Gly Val Thr Asp Gly Gly Val Gly Pro Leu Leu Gln Gln Gly Asp
                245                 250                 255

Val Ser Ser Ser Lys Pro Ala Leu Leu Asp Thr Gln Leu Leu Gly Thr
            260                 265                 270

Phe Leu Leu Glu Ala Leu Asp Gly Phe Leu Phe Val Val Asn Thr Glu
        275                 280                 285

Gly Lys Thr Glu Tyr Val Ser Glu Asn Val Ala His Phe Leu His Tyr
    290                 295                 300

Gln Pro Gln Asp Leu Val Gly Lys Ser Ile Tyr Asn Phe Ile His His
305                 310                 315                 320

Gly Asp His Ala Arg Phe Ser Ser Ser Leu Leu Pro Thr Ala Ile Ala
                325                 330                 335

Trp Pro Ser Glu Met Ala Pro Thr Ser Gln Asn Arg Ile Gly Arg Cys
            340                 345                 350

Phe Asn Cys Arg Leu Leu Ile Gln Pro Leu Gly Glu Gln Asp Glu Thr
        355                 360                 365

Met Glu Glu Lys Gln Gln Arg Val Glu His Tyr Glu Asn Met Gln Ile
    370                 375                 380

Ser Ala Val Leu Gln Pro Tyr Pro Ala Asp Gly Gly Gln Gln Gln Gln
385                 390                 395                 400

Gln Pro Thr Lys Lys Ile Ser Gly Ala Ala Ala Ala Ala Ala Ala Ala
                405                 410                 415

Ala Ala Ala Val Gly Leu Glu Thr Ser Asp Leu Glu Leu Ala Leu Thr
            420                 425                 430

Ser Val Ala Ser Gly Ser Leu Ala Gly Asp Pro Gln His Cys Leu Val
        435                 440                 445

Cys Val Ala Arg Arg Ile Pro Ser Thr Glu Lys Met Ala Ala Ala Asn
    450                 455                 460

Pro Thr Val Gly Gly Pro Ile Val Glu Gln Phe Thr Thr Lys Leu Asp
465                 470                 475                 480

Pro Ser Gly Lys Ile Val Ala Val Asp Val Thr Gly Val Ser Ser Pro
                485                 490                 495

Tyr Ser Ser Tyr Leu Ser Lys Glu Ala Leu Val Ser Cys Thr Ile Gln
            500                 505                 510

Glu Leu Cys Tyr Pro Asp Asp Leu Pro Val Phe Gln Ala His Leu Gln
        515                 520                 525

Glu Thr Leu His Ser Gly Cys Gly Ile Ser Ser Arg Tyr Arg Leu Arg
    530                 535                 540

Leu Thr Gly Ala Ser Thr Pro Met Gly His Arg Gly Gly Ala Gly Gly
545                 550                 555                 560

Gly Ser Gly Gly Phe Leu Val Val Gln Thr Lys Ser Lys Arg Phe Ile
                565                 570                 575

His Gly Asp Thr His Glu Thr Asp Phe Ile Met Ala Thr His Ser Ile
            580                 585                 590

Ile Val Asp Asp Asp Gly Glu Asp Val Asp Thr Gly Asn Ser Ser Ser
        595                 600                 605

Ser Asn Thr Asn Thr Asn Thr Ser Arg Met Met Leu Leu Ala Ala Ala
    610                 615                 620
```

```
Ser Asp Thr Leu Asn Asp His His Arg Leu Ser Glu Ser Thr Gly Ser
625                 630                 635                 640

Ile Ile Ser Gln Pro Gln Gln Gln Gln Gln Gln Gln Gln Gln Gln Gln
                645                 650                 655

Gln Gln Gln Gln Ser Asn Pro Val Leu Thr Ser Val Val Arg His Asp
            660                 665                 670

Val Ile Ser Ala Thr Ser Phe Gly Asn Ser Gly Cys Ser Gly Gly Ala
        675                 680                 685

Thr Thr Ala Thr Thr Ser Ser Thr Ser Ser Ser Ser Tyr Ser Ser Thr
    690                 695                 700

Phe Ala Gly Leu Ser Leu Gly Thr Ser Gly Asp Leu Leu Asn Asp Phe
705                 710                 715                 720

Val Val Pro Asp Leu Phe Met Ala Ser Pro Pro Trp Asp Phe Asn Asn
                725                 730                 735

Ser Glu Ser Ser Leu Asp Asp Gly Gly Ser Gly Val Ala Leu Ala Ala
            740                 745                 750

Ala Ser Ala Ala Ala Ser Ala Ala Val Ala Ala Ala Ala Gln Ile Thr
        755                 760                 765

Asn Ser His His Leu Gln Ala Val Thr Ala Thr Ser Ser Leu Gln Leu
    770                 775                 780

Ser Val Pro Ser Pro Leu Ser Leu Ile Pro Ser Gly Gly Pro Leu Leu
785                 790                 795                 800

Ala Gly His Leu Pro His His Ser Val Gly Gly Met Ile Asn Trp Gly
                805                 810                 815

Ser Pro Pro Pro Ser Ala Gly Ala Gly Gly Val Gly Gln Arg Ala Gly
            820                 825                 830

Ser Thr Pro Cys Gly Gln Met Ala Thr Val Met Gly Ser Ser Arg Pro
        835                 840                 845

Ser Ser Arg Gln Ser Ala Ser Ser Thr Pro Arg Pro Pro Ser Val Ser
    850                 855                 860

Ser Ala Phe Ser Pro Ala Pro Asn Ser Val Leu Gly Val Val His Pro
865                 870                 875                 880

Ser Pro Val Leu Ser Pro Val Gly Ala Thr Ser Ile His Ser Ala Ala
                885                 890                 895

Met Ser Cys Thr Ser Gly Leu Val Thr Gly Ser Thr Ser Ser Ser Ser
            900                 905                 910

Ala Gly Gln Gln Gln Pro Ser Pro Ala Ser Met Thr Thr Pro Phe Ser
        915                 920                 925

Asn Asn Phe Pro Phe Ser Pro Leu Gln Asp Pro Ile Pro Gln His Pro
    930                 935                 940

Ala Thr Ala Pro Gln Thr His Asn Pro Ala Thr Pro Phe Leu Asp Glu
945                 950                 955                 960

Val Arg Asp Thr Lys Asp Gly Ile Ile Ser Ser Gly Pro Gly Gly Ser
                965                 970                 975

Val Ser His Gly His Asn Tyr Leu Ser Gly Gly Ser His His Gln Gln
            980                 985                 990

Gln His His His His His Gln Gln  Gln Gln Gln Gln Gln  Gln Gln Gln
        995                 1000                1005

Gln His  Ala Thr Asp Lys Gln  Met Ser Ala Leu Ser  Ser Leu Leu
    1010                1015                1020

Asn Cys  Asn Asp Ala Ala Thr  Ser Ser Ser Ser Ser  Ser Ser Ser
    1025                1030                1035
```

-continued

```
Ser Ser  Ser Ser Ser Ser Ser  Ser Ser Leu Ala Glu  Ser Gly Arg
    1040                 1045                 1050

Leu Arg  Ile Leu Leu Met Gln  Arg Pro Gly Asn Ala  Pro Pro Pro
    1055                 1060                 1065

Ser Ala  His Gln Gln Pro Gly  His Ser Ser Ser Gly  Ser Ser Ser
    1070                 1075                 1080

Ser Ser  Ser Ser Thr Ser Thr  Ser Thr Ser Thr Ser  Thr Ser Thr
    1085                 1090                 1095

Ser Thr  Asn Thr Asn Thr Asn  Thr Asn Ser Ser Asn  Asn Asn Asn
    1100                 1105                 1110

Asn Asn  Asn Asn Asn Ala Ser  Gly Asn Asn Asn Ser  Ser Ser Val
    1115                 1120                 1125

Asn Gly  Ser His Leu Leu Ala  Ala Leu Gly Asp Ala  Glu Ala Val
    1130                 1135                 1140

Lys Arg  Glu Lys Asp Glu Asn  Ser Gly Ala Pro Ser  Cys Gly Ser
    1145                 1150                 1155

Leu Ser  Val Thr Lys Gly Ser  His Gly Asn Arg Ile  Leu Lys Gly
    1160                 1165                 1170

Leu Leu  Asn Gln Asp Asp Gly  Asp Glu Ala Asp Gln  Ala Asp Asp
    1175                 1180                 1185

Thr Ser  Asn His Arg Phe Leu  Leu Thr Ala Arg Gly  Asn Leu Ser
    1190                 1195                 1200

Gly Asp  Gly Val Lys Thr Ser  Ser Ser Ala Gly Asn  Asn Asn Asn
    1205                 1210                 1215

Asn Thr  Thr Asn Thr Asn Asn  Asn Asn Thr Asn Asn  Asn Asn Asn
    1220                 1225                 1230

Met Leu  His Lys Leu Leu Asn  Val Arg Ser Asp Asp  Asp Ala Glu
    1235                 1240                 1245

Gln Arg  Met Gly Leu Arg Lys  Pro Asn Glu Leu Leu  Lys Lys Leu
    1250                 1255                 1260

Leu Lys  Asp Pro Glu Glu Asp  His Gln Gln Ala Ser  Gly Asn Gly
    1265                 1270                 1275

Ser Ser  Ser Ala Cys Gly Gly  Thr Gly Ser Gly Gly  Thr Ala Asn
    1280                 1285                 1290

Gln Leu  Gln Gln Phe His His  Gln Arg Gln Gln Gln  Gln Gln Gln
    1295                 1300                 1305

Gln Gln  Gln His Gln Gln His  Gln Gln His Gln Gln  His Gln Gln
    1310                 1315                 1320

Ser Gln  Gln Gln Gln Gln Gln  Asn Gln His His His  Ser Asp Gln
    1325                 1330                 1335

Val Ser  Phe Gln Glu Glu Gln  Leu Leu Lys Ser Phe  Gly Phe Pro
    1340                 1345                 1350

Ser Pro  Thr Ala Ser Ser Gly  Ser Ser Thr Ala Ala  Thr Val Ala
    1355                 1360                 1365

Thr Gly  Ser Leu Ala Asn Met  Leu Ala Thr Ser Gln  Met Thr His
    1370                 1375                 1380

Leu Arg  Ser Pro Gln Pro Pro  Gly Met Ser Ser His  Cys Asp Gly
    1385                 1390                 1395

Leu Leu  Glu Phe Gly Gly Val  Val Cys Ser Ser Thr  Thr Ala Ser
    1400                 1405                 1410

Gly Met  Val Phe Gly Gly Asn  Ala Ala Val Gly Gly  Ala Ser Gly
    1415                 1420                 1425

Met Arg  Gly Thr Lys Arg His  Ser Glu Glu Ala Arg  Asp Glu Val
```

```
    1430                1435                1440

Lys Ala  Ser Lys Glu Pro Met  Leu Ser Ala Asp His  Leu Met Met
    1445                1450                1455

Ser Ala  Gly Gly Gly Gly Val  Leu His Gln Leu Leu  Gly Pro Pro
    1460                1465                1470

Pro Leu  Ser Thr Ala Ser Thr  Ser Ser Ser Ser Ser  Ala Ser Ser
    1475                1480                1485

Ser Ser  Ala Cys Ser Ser Ser  Ala Ala Leu Ser Ser  Ser Leu Ala
    1490                1495                1500

Pro Ser  Asn Ala His Ser Val  Ala Ala Thr Thr Leu  Ala Ile Ala
    1505                1510                1515

Ala Leu  Gln His Gln Pro Leu  Ser Ser Pro Ser Thr  Ala Ala Ala
    1520                1525                1530

Val Ala  Ala Ala Thr Ser Ala  Val Ala Ala Ala Ala  Ala Thr Ala
    1535                1540                1545

Asn Ala  Met Ala Ser Gln Leu  Gln Ala Ala Pro Ser  Ala Gln Ser
    1550                1555                1560

Ala Ala  Ala Ala Val Ala Ala  Ala Ala Ala Ala Ala  Ala Ala Ala
    1565                1570                1575

Ala Ala  Ala Ala Ala Ala Asn  Leu Pro Ala Ser Ser  Lys Leu Cys
    1580                1585                1590

Glu Lys  Asn Lys Met Leu Ala  Ser Leu Leu Ala Lys  Thr Pro Val
    1595                1600                1605

Met Pro  Ser Pro Ser Ser Thr  Asn Ile Ala Ser Pro  Lys Pro Ser
    1610                1615                1620

Ala Leu  Pro Gln Glu Lys Leu  Pro Lys Asp Leu Lys  Glu Lys Ile
    1625                1630                1635

Leu Gln  Thr Pro Pro Val Ser  Gly Thr Ser Ala Pro  Gly Ala His
    1640                1645                1650

Trp Ala  Gly Gly Ser Val Gln  Thr Gln Pro Pro Thr  Thr Met Gln
    1655                1660                1665

Leu Pro  Pro His Pro Ala Ile  Gln Gln Pro Gln Gln  Gln Gln Gln
    1670                1675                1680

His Val  Leu Asn Gln Gln Gln  Gln Gln Gln Gln Gln  Gln Gln Gln
    1685                1690                1695

Gln Gln  Gln Gln Gln Gln Gln  Gln Gln Gln Gln Gln  Gln Gln Gln
    1700                1705                1710

Gln Arg  His Pro Ala Met Gln  Gln Ser Gln Gln His  Gln Leu His
    1715                1720                1725

Pro Arg  Ser Gln His Leu Pro  Gln Gln His Gln His  Leu Asn Leu
    1730                1735                1740

Gly Gln  Lys Gln Gln Gln Gln  Pro Thr Pro Gln Thr  Gly Gly Phe
    1745                1750                1755

Leu Asn  Ser Leu Leu Asn Arg  Pro Ile Asp Ser Ala  Ser Gly Pro
    1760                1765                1770

Asn Ile  Ile Gly Glu Ser Gln  Gln Gln Ala Asn Gln  Gln Gln Gln
    1775                1780                1785

Gln Gln  Gln Gln Gln Gln Gln  Gln Gln Leu Tyr Leu  Ala Ala Gln
    1790                1795                1800

Gln Pro  Pro Pro Val Gln Leu  Gln His Arg Pro Asn  Gln Thr Val
    1805                1810                1815

Gln Lys  Leu Ser Leu Asn Asn  Gln Gln Gln Leu Ser  Ala Ala Met
    1820                1825                1830
```

```
Asn Ser  Ser Gly Gly Phe Asn  Ile Ser Leu His Pro  Gln Gln His
    1835                 1840                 1845

Gln Gln  Gln Gln Gln Gln His  His His His Leu Gln  Gln Gln Gln
    1850                 1855                 1860

Gln Gln  Gln Gln Gln His His  Gln Gln Gln Gln Gln  Gln Gln Gln
    1865                 1870                 1875

Gln Gln  Gln Gln Gln Gln Gln  Gln Gln Gln Gln Gln  His His Gln
    1880                 1885                 1890

Leu Gln  His Gln Leu Ser Gly  Ser Met Leu Ala Asp  Arg Gly Leu
    1895                 1900                 1905

Leu Gln  Ala Gly Gly Gly Pro  Gly Gln Arg Ser Gly  Met Ser Ile
    1910                 1915                 1920

Gln Pro  Gln Gln Gln Thr Ser  His Ala Asn Ser Met  Ile Ala Ala
    1925                 1930                 1935

Ala Ser  Leu Glu Ser Ser Asp  Gly Ser Tyr Ser Val  His Ala Asp
    1940                 1945                 1950

Phe Met  Thr Pro Leu Asp Val  Gln Met Ala Ser Val  Ala Gly Trp
    1955                 1960                 1965

Gly Asp  Thr Pro Ser Met Asp  Pro Glu Leu Ser Asp  Ile Ile Glu
    1970                 1975                 1980

Gln Val  Ile Asp Met Asp Glu  Arg Tyr Glu Ser Asp  Ser Met Ile
    1985                 1990                 1995

Phe Gly  Glu Leu Thr Ser Val  Thr Pro Pro Pro Val  Ala Ile Gln
    2000                 2005                 2010

Pro Val  Leu Ser Val Gln Ser  Ser Gln Ala Ile Ala  Ser Val Ala
    2015                 2020                 2025

Gln Ala  Thr Ala Ile Val Gly  Pro Leu Gly Pro His  Leu Gln Met
    2030                 2035                 2040

Asp Met  Ser Lys Glu Lys Leu  Ala Ile Thr Ala Ile  Gln Lys Ser
    2045                 2050                 2055

Leu Met  Ser Tyr Glu Lys Ile  Pro Thr Val Ala Gln  Ser Pro Pro
    2060                 2065                 2070

Ala Tyr  Asn Leu Pro Gly Tyr  Ala Gln Gln Gly Gln  Gly Ala Pro
    2075                 2080                 2085

Thr Arg  Met Ser Thr Pro Thr  Tyr Gly Met Asn Ser  Ala Pro Ala
    2090                 2095                 2100

Ser Ser  Leu Pro Met Ala Asn  Gln Gln Leu Gln Thr  Asn Leu Thr
    2105                 2110                 2115

Met Pro  Gly Ala Arg Lys Gln  Lys Leu Pro Val Gln  Gln Arg Arg
    2120                 2125                 2130

Leu Ala  Asn Arg Gln Gln Gln  Gln Gln Gln Gln Gln  Gln Gln Gln
    2135                 2140                 2145

Gln Gln  Gln Gln Gln Gln Gln  Gln Gln Gln Gln Gln  Gln Gln Gln
    2150                 2155                 2160

Ser Ser  Ser Gln Glu Gln Gln  Gln Gln Gln Gln Gln  Pro Ala Pro
    2165                 2170                 2175

Gln Gln  Gln Leu Leu Gly Val  Leu Leu Asn Glu Ser  Ser Val Gln
    2180                 2185                 2190

His Thr  Gln Gly Ala Gln Leu  Ser Pro Gly Ala Leu  Gln Ile Met
    2195                 2200                 2205

Asp Asp  Leu Leu Asn Ala Ile  Pro Pro Asn Met Thr  Ile Ser Arg
    2210                 2215                 2220
```

<210> SEQ ID NO 15
<211> LENGTH: 101
<212> TYPE: DNA
<213> ORGANISM: Artificial
<220> FEATURE:
<223> OTHER INFORMATION: Synthetic DNA

<400> SEQUENCE: 15
ctagtccatt ttccattccc atgtgcagaa tgtgcgaaaa acgttgcacg tcctctcgat 60
ggcgtcgaaa atcgttgcac ggccgccacg cgaactctgc t 101

<210> SEQ ID NO 16
<211> LENGTH: 101
<212> TYPE: DNA
<213> ORGANISM: Artificial
<220> FEATURE:
<223> OTHER INFORMATION: Synthetic DNA

<400> SEQUENCE: 16
ctagagcaga gttcgcgtgg cggccgtgca acgattttcg acgccatcga gaggacgtgc 60
aacgtttttc gcacattctg cacatgggaa tggaaaatgg a 101

<210> SEQ ID NO 17
<211> LENGTH: 78
<212> TYPE: DNA
<213> ORGANISM: Artificial
<220> FEATURE:
<223> OTHER INFORMATION: Synthetic DNA

<400> SEQUENCE: 17
aataggggtt ccgcgcacat ttccccgaaa agtgccacct attaccctgt tatccctagg 60
tccttttcat cacgtgct 78

<210> SEQ ID NO 18
<211> LENGTH: 78
<212> TYPE: DNA
<213> ORGANISM: Artificial
<220> FEATURE:
<223> OTHER INFORMATION: Synthetic DNA

<400> SEQUENCE: 18
tatttttata ggttaatgtc atgataataa tggtttctta tagggataac agggtaatag 60
gacggatcgc ttgcctgt 78

<210> SEQ ID NO 19
<211> LENGTH: 72
<212> TYPE: DNA
<213> ORGANISM: Artificial
<220> FEATURE:
<223> OTHER INFORMATION: Synthetic DNA

<400> SEQUENCE: 19
tttgcgtcca tccaaaaaaa aagtaagaat ttttgaaagg ggatccaaca aaatggacaa 60
aatgagcgag ac 72

<210> SEQ ID NO 20
<211> LENGTH: 60
<212> TYPE: DNA
<213> ORGANISM: Artificial
<220> FEATURE:
<223> OTHER INFORMATION: Synthetic DNA

<400> SEQUENCE: 20
cggttagagc ggatgtggga ggagggcgtg aatgtaagct tctatgcact gttggttcca 60

<210> SEQ ID NO 21
<211> LENGTH: 40
<212> TYPE: DNA
<213> ORGANISM: Artificial
<220> FEATURE:
<223> OTHER INFORMATION: Synthetic DNA

<400> SEQUENCE: 21
cccccccggg aacaaaatgg cagcaccaga gacgggcaac 40

<210> SEQ ID NO 22
<211> LENGTH: 35
<212> TYPE: DNA
<213> ORGANISM: Artificial
<220> FEATURE:
<223> OTHER INFORMATION: Synthetic DNA

<400> SEQUENCE: 22
ccccgaattc ctcatcgcag cgtgctggtc agggt 35

<210> SEQ ID NO 23
<211> LENGTH: 73
<212> TYPE: DNA
<213> ORGANISM: Artificial
<220> FEATURE:
<223> OTHER INFORMATION: Synthetic DNA

<400> SEQUENCE: 23
tttgaaaatt cgaattcaac cctcactaaa gggcggccgc actagtaaaa acatgctgac 60
ggataccgca ttc 73

<210> SEQ ID NO 24
<211> LENGTH: 69
<212> TYPE: DNA
<213> ORGANISM: Artificial
<220> FEATURE:
<223> OTHER INFORMATION: Synthetic DNA

<400> SEQUENCE: 24
cttgattgga gacttgacca aacctctggc gaagaattgt taattaatta cctggatatc 60
gtcatgttg 69

<210> SEQ ID NO 25
<211> LENGTH: 43
<212> TYPE: DNA
<213> ORGANISM: Artificial
<220> FEATURE:
<223> OTHER INFORMATION: Synthetic DNA

<400> SEQUENCE: 25
caaagaaaat acgcagggcc cgcggcacgt gtgtgcatcc cat 43

<210> SEQ ID NO 26
<211> LENGTH: 49
<212> TYPE: DNA
<213> ORGANISM: Artificial
<220> FEATURE:
<223> OTHER INFORMATION: Synthetic DNA

<400> SEQUENCE: 26
ctagtcaaag aaaatacgca gggcccgcgg cacgtgtgtg catcccatt 49

<210> SEQ ID NO 27
<211> LENGTH: 49
<212> TYPE: DNA
<213> ORGANISM: Artificial
<220> FEATURE:
<223> OTHER INFORMATION: Synthetic DNA

<400> SEQUENCE: 27
ctagaatggg atgcacacac gtgccgcggg ccctgcgtat tttctttga 49

<210> SEQ ID NO 28
<211> LENGTH: 43
<212> TYPE: DNA
<213> ORGANISM: Artificial
<220> FEATURE:
<223> OTHER INFORMATION: Synthetic DNA

<400> SEQUENCE: 28
caaagaaaat acgcacacgc ggcggaggcc ttgtgcatcc cat 43

<210> SEQ ID NO 29
<211> LENGTH: 49
<212> TYPE: DNA
<213> ORGANISM: Artificial
<220> FEATURE:
<223> OTHER INFORMATION: Synthetic DNA

<400> SEQUENCE: 29
ctagtcaaag aaaatacgca cacgcggcgg aggccttgtg catcccatt 49

<210> SEQ ID NO 30
<211> LENGTH: 49
<212> TYPE: DNA
<213> ORGANISM: Artificial
<220> FEATURE:
<223> OTHER INFORMATION: Synthetic DNA

<400> SEQUENCE: 30
ctagaatggg atgcacaagg cctccgccgc gtgtgcgtat tttctttga 49

<210> SEQ ID NO 31
<211> LENGTH: 43
<212> TYPE: DNA
<213> ORGANISM: Artificial
<220> FEATURE:
<223> OTHER INFORMATION: Synthetic DNA

<400> SEQUENCE: 31
caaagaaaat acgcagggcc cgcggaggcc ttgtgcatcc cat 43

<210> SEQ ID NO 32
<211> LENGTH: 49
<212> TYPE: DNA
<213> ORGANISM: Artificial
<220> FEATURE:
<223> OTHER INFORMATION: Synthetic DNA

<400> SEQUENCE: 32
ctagtcaaag aaaatacgca gggcccgcgg aggccttgtg catcccatt 49

<210> SEQ ID NO 33
<211> LENGTH: 49
<212> TYPE: DNA
<213> ORGANISM: Artificial
<220> FEATURE:
<223> OTHER INFORMATION: Synthetic DNA

<400> SEQUENCE: 33
ctagaatggg atgcacaagg cctccgcggg ccctgcgtat tttctttga 49

<210> SEQ ID NO 34
<211> LENGTH: 22
<212> TYPE: DNA
<213> ORGANISM: Daphnia magna

<400> SEQUENCE: 34
gcacacgcgg cggcacgtgt gt 22

<210> SEQ ID NO 35
<211> LENGTH: 28
<212> TYPE: DNA
<213> ORGANISM: Artificial
<220> FEATURE:
<223> OTHER INFORMATION: Synthetic DNA

<400> SEQUENCE: 35
ctagtgcaca cgcggcggca cgtgtgtt 28

<210> SEQ ID NO 36
<211> LENGTH: 28
<212> TYPE: DNA
<213> ORGANISM: Artificial
<220> FEATURE:
<223> OTHER INFORMATION: Synthetic DNA

<400> SEQUENCE: 36
ctagaacaca cgtgccgccg cgtgtgca 28

<210> SEQ ID NO 37
<211> LENGTH: 36
<212> TYPE: DNA
<213> ORGANISM: Daphnia magna

<400> SEQUENCE: 37
aaaatacgca cacgcggcgg cacgtgtgtg catccc 36

<210> SEQ ID NO 38
<211> LENGTH: 42
<212> TYPE: DNA
<213> ORGANISM: Artificial
<220> FEATURE:
<223> OTHER INFORMATION: Synthetic DNA

<400> SEQUENCE: 38
ctagtaaaat acgcacacgc ggcggcacgt gtgtgcatcc ct 42

<210> SEQ ID NO 39
<211> LENGTH: 42
<212> TYPE: DNA
<213> ORGANISM: Artificial
<220> FEATURE:
<223> OTHER INFORMATION: Synthetic DNA

<400> SEQUENCE: 39
ctagagggat gcacacacgt gccgccgcgt gtgcgtattt ta 42

<210> SEQ ID NO 40
<211> LENGTH: 43
<212> TYPE: DNA
<213> ORGANISM: Artificial
<220> FEATURE:

<223> OTHER INFORMATION: Synthetic DNA

<400> SEQUENCE: 40
caaagaaaat actaccacgc ggcggcacgt gtgtgcatcc cat 43

<210> SEQ ID NO 41
<211> LENGTH: 49
<212> TYPE: DNA
<213> ORGANISM: Artificial
<220> FEATURE:
<223> OTHER INFORMATION: Synthetic DNA

<400> SEQUENCE: 41
ctagtcaaag aaaatactac cacgcggcgg cacgtgtgtg catcccatt 49

<210> SEQ ID NO 42
<211> LENGTH: 49
<212> TYPE: DNA
<213> ORGANISM: Artificial
<220> FEATURE:
<223> OTHER INFORMATION: Synthetic DNA

<400> SEQUENCE: 42
ctagaatggg atgcacacac gtgccgccgc gtggtagtat tttctttga 49

<210> SEQ ID NO 43
<211> LENGTH: 43
<212> TYPE: DNA
<213> ORGANISM: Artificial
<220> FEATURE:
<223> OTHER INFORMATION: Synthetic DNA

<400> SEQUENCE: 43
caaagaaaat acgcacacgc ggcggcacgt ggtggcatcc cat 43

<210> SEQ ID NO 44
<211> LENGTH: 49
<212> TYPE: DNA
<213> ORGANISM: Artificial
<220> FEATURE:
<223> OTHER INFORMATION: Synthetic DNA

<400> SEQUENCE: 44
ctagtcaaag aaaatacgca cacgcggcgg cacgtggtgg catcccatt 49

<210> SEQ ID NO 45
<211> LENGTH: 49
<212> TYPE: DNA
<213> ORGANISM: Artificial
<220> FEATURE:
<223> OTHER INFORMATION: Synthetic DNA

<400> SEQUENCE: 45
ctagaatggg atgccaccac gtgccgccgc gtgtgcgtat tttctttga 49

<210> SEQ ID NO 46
<211> LENGTH: 43
<212> TYPE: DNA
<213> ORGANISM: Artificial
<220> FEATURE:
<223> OTHER INFORMATION: Synthetic DNA

<400> SEQUENCE: 46
caaagaaaat actaccacgc ggcggcacgt ggtggcatcc cat 43

<210> SEQ ID NO 47
<211> LENGTH: 49
<212> TYPE: DNA
<213> ORGANISM: Artificial
<220> FEATURE:
<223> OTHER INFORMATION: Synthetic DNA

<400> SEQUENCE: 47
ctagtcaaag aaaatactac cacgcggcgg cacgtggtgg catcccatt 49

<210> SEQ ID NO 48
<211> LENGTH: 49
<212> TYPE: DNA
<213> ORGANISM: Artificial
<220> FEATURE:
<223> OTHER INFORMATION: Synthetic DNA

<400> SEQUENCE: 48
ctagaatggg atgccaccac gtgccgccgc gtggtagtat tttctttga 49

<210> SEQ ID NO 49
<211> LENGTH: 43
<212> TYPE: DNA
<213> ORGANISM: Artificial
<220> FEATURE:
<223> OTHER INFORMATION: Synthetic DNA

<400> SEQUENCE: 49
caaagaaaat acgcacacgc gtattcacgt gtgtgcatcc cat 43

<210> SEQ ID NO 50
<211> LENGTH: 49
<212> TYPE: DNA
<213> ORGANISM: Artificial
<220> FEATURE:
<223> OTHER INFORMATION: Synthetic DNA

<400> SEQUENCE: 50
ctagtcaaag aaaatacgca cacgcgtatt cacgtgtgtg catcccatt 49

<210> SEQ ID NO 51
<211> LENGTH: 49
<212> TYPE: DNA
<213> ORGANISM: Artificial
<220> FEATURE:
<223> OTHER INFORMATION: Synthetic DNA

<400> SEQUENCE: 51
ctagaatggg atgcacacac gtgaatacgc gtgtgcgtat tttctttga 49

<210> SEQ ID NO 52
<211> LENGTH: 43
<212> TYPE: DNA
<213> ORGANISM: Artificial
<220> FEATURE:
<223> OTHER INFORMATION: Synthetic DNA

<400> SEQUENCE: 52
caaagaaaat actaccacgc gtattcacgt ggtggcatcc cat 43

<210> SEQ ID NO 53
<211> LENGTH: 49
<212> TYPE: DNA
<213> ORGANISM: Artificial
<220> FEATURE:
<223> OTHER INFORMATION: Synthetic DNA -continued

```
<400> SEQUENCE: 53

ctagtcaaag aaaatactac cacgcgtatt cacgtggtgg catcccatt              49


<210> SEQ ID NO 54
<211> LENGTH: 49
<212> TYPE: DNA
<213> ORGANISM: Artificial
<220> FEATURE:
<223> OTHER INFORMATION: Synthetic DNA

<400> SEQUENCE: 54

ctagaatggg atgccaccac gtgaatacgc gtggtagtat tttctttga              49
```

NUCLEIC ACID THAT INTERACTS WITH A RECEPTOR FOR ENDOCRINE DISRUPTING CHEMICALS AND USE THEREOF

TECHNICAL FIELD

The present invention relates to a nucleic acid that interacts with a receptor for endocrine disrupting chemicals; i.e., a nucleic acid that is responsive to endocrine disrupting chemicals via a receptor for endocrine disrupting chemicals, a vector and a transformant comprising such nucleic acid, and a method for evaluating a test substance using such nucleic acid.

BACKGROUND ART

Endocrine disrupting chemicals are substances that may disrupt endocrine actions of organisms and induce, for example, impairment of reproductive functions or malignant tumors. Endocrine disrupting chemicals are also referred to as "hormonally active agents." Even if the amount thereof incorporated into an organism is very small, endocrine disrupting chemicals would adversely affect normal hormone actions. Endocrine disrupting chemicals exert actions on organisms by, for example, binding to receptors to which hormones should bind in nature. Actions exerted by endocrine disrupting chemicals on organisms may be hormone-like actions or actions opposite thereto.

For example, components of agricultural chemicals, insecticides, coating materials, corrosion inhibitors, and the like include compounds that are known as endocrine disrupting chemicals exerting estrogen-like actions or androgen-like actions, and influence thereof on humans has been an issue of concern.

Meanwhile, chemicals that regulate functions of juvenile hormones (JHs) peculiar to arthropods are developed as insecticides. Juvenile hormones are characteristic hormones that regulate metamorphosis and reproduction of a variety of arthropods. When a methoprene-tolerant (MET) receptor (a Gce (germ-cell-expressed) receptor also exists in a fruit fly) accepts juvenile hormones, in the case of insects, the final form of physiological functions are exerted by activating transcription of the downstream Kruppel homolog 1 (Kr-hl). When juvenile hormones do not function normally, accordingly, arthropods having juvenile hormones cannot survive. Since mammalian animals do not have juvenile hormones, use of chemicals that regulate functions of juvenile hormones as insecticides on humans had been considered to be highly safe. There are several types of juvenile hormones. In many insects of *Coleoptera, Hymenoptera, Diptera*, and the like, JHIII is known, JH and JHII are known in *Lepidoptera*, and methyl farnesoate is known in *Crustacea.*

For example, Patent Literature 1 discloses that a response element that activates transcription of a downstream gene in response to juvenile hormones (JHs) (i.e., a juvenile hormone response element (a JH response element)) was discovered in silk worm and that a reporter assay for evaluating JH responsiveness was developed with the use of the JH response element in combination with a reporter gene. Such JH response element comprises CACGTG nucleotides referred to as an E-box. In addition, CACGCG that is located upstream of Kr-hl and referred to as a C-box is found to function as a JH response element (Non-Patent Literature 1).

In general, daphnid produces only female offspring by parthenogenesis. Upon environmental deterioration, however, daphnid is known to produce male offspring, be fertilized, and produce eggs that are tolerant to environmental changes referred to as "resisting eggs." When daphnid is exposed to juvenile hormones or juvenile hormonally active agents or when the amount of juvenile hormones in the daphnid body is increased, *Crustacea* such as daphnid using, as a juvenile hormone, a JHIII precursor methyl farnesoate is reported to produce male offspring (Non-Patent Literature 2 and Non-Patent Literature 3). Thus, a substance that acts as a ligand to a juvenile hormone receptor or that inhibits functions of a juvenile hormone receptor can be considered as endocrine disrupting chemicals.

As a method for evaluating actions of juvenile hormones, a reproduction test that is carried out with the use of *Daphnia magna* is available. However, such reproduction test is disadvantageous in terms of the necessity of a long test period and the necessity of techniques for breeding and evaluation (Non-Patent Literature 4). While a system for evaluating actions of juvenile hormones with the use of cultured cells has been established, such system is disadvantageous in terms of the necessity of techniques for breeding and subculture. In addition, Non-Patent Literature 5 and Non-Patent Literature 6 disclose candidate nucleotide sequences of the juvenile hormone receptor gene (the MET gene) and the JH response element of *Daphnia magna*, although a practical evaluation system has not yet been developed.

PRIOR ART LITERATURE

Patent Literature 1: JP Patent 5,754,681

NON-PATENT LITERATURES

Non-Patent Literature 1: Qianyu He, et al., Heat Shock Protein 83 (Hsp83) Facilitates Methoprene-tolerant (Met) Nuclear Import to Modulate Juvenile Hormone Signaling Journal of Biological Chemistry, 289, 2014, pp. 27874-27885

Non-Patent Literature 2: Norihisa Tatarazako, et al., Juvenile hormone agonists affect the occurrence of male *Daphnia*, Chemosphere, 53, 2003, pp. 827-833

Non-Patent Literature 3: Kenji Toyota, et al., Methyl farnesoate synthesis is necessary for the environmental sex determination in the water flea *Daphnia pulex*, Journal of Insect Physiology, 80, 2015, pp. 22-30

Non-Patent Literature 4: Helen Ying Wang, et al., The screening of chemicals for juvenoid-related endocrine activity using the water flea *Daphnia magna*, Aquatic Toxicology 74, 2005, pp. 193-204

Non-Patent Literature 5: Tomas A. Gorr, et al., A candidate juvenoid hormone receptor cis-element in the *Daphnia magna* hb2 hemoglobin gene promoter, Molecular and Cellular Endocrinology 247, 2006, pp. 91-102

Non-Patent Literature 6: Nur Syafiqah Mohamad Ishak, et al., Co-option of the bZIP transcription factor Vrille as the activator of Doublesex 1 in environmental sex determination of the crustacean *Daphnia magna* 13, 2017, e1006953

SUMMARY OF THE INVENTION

Objects to be Attained by the Invention

As described above, there are endocrine disrupting chemicals for each of various hormones including juvenile hormones. Accordingly, it was necessary to prepare an evaluation system for each of various hormones to examine endocrine disrupting actions of a particular compound. In order to evaluate endocrine disrupting actions of a particular compound, as described above, a large number of steps was necessary, and a cost of evaluation was increased, disadvantageously. In addition, a very small amount of endocrine disrupting chemicals would adversely affect organisms as described above. Accordingly, development of an evaluation system that enables highly sensitive detection of endocrine disrupting actions of a very small amount of endocrine disrupting chemicals is awaited.

Under the above circumstances, it is an object of the present invention to provide a nucleic acid that can be used in a highly sensitive evaluation system that can detect various endocrine disrupting actions in a very small amount of endocrine disrupting chemicals, a vector and a transformant comprising such nucleic acid, and a method for evaluating a test substance using such nucleic acid.

Means for Attaining the Objects

The present inventors have conducted concentrated studies in order to attain the above objects. As a result, they succeeded in identifying a nucleic acid that is excellent in responsiveness to various endocrine disrupting chemicals. This has led to the completion of the present invention.

The present invention encompasses the following.

(1) A nucleic acid comprising a total of 20 to 60 nucleotides comprising the nucleotide sequence shown in SEQ ID NO: 1.

(2) The nucleic acid according to (1), wherein arbitrary 4 nucleotides (nnnn) comprised in the nucleotide sequence shown in SEQ ID NO: 1 are kmkk, provided that k indicates g or t and m indicates a or c.

(3) The nucleic acid according to (1), wherein arbitrary 4 nucleotides (nnnn) comprised in the nucleotide sequence shown in SEQ ID NO: 1 are GCGG or TATT.

(4) The nucleic acid according to any of (1) to (3), which comprises nucleotide sequences of given nucleotide lengths on the 3' terminal side and the 5' terminal side of the nucleotide sequence shown in SEQ ID NO: 1.

(5) The nucleic acid according to (1), which consists of a nucleotide sequence selected from the group consisting of SEQ ID NOs: 2, 5, 8, 34, 37, 40, 43, 46, 49, and 52.

(6) A vector comprising the nucleic acid according to any of (1) to (5).

(7) The vector according to (6), wherein the nucleic acid is designated as a unit and a plurality of units of the nucleic acids are bound to each other.

(8) The vector according to (6), which comprises a reporter gene on the 3' terminal side of a sense strand of the nucleic acid.

(9) A transformant comprising the nucleic acid according to any of (1) to (5) introduced into a host.

(10) The transformant according to (9), wherein the nucleic acid is designated as a unit and a plurality of units of the nucleic acids are bound to each other.

(11) The transformant according to (9), which comprises a reporter gene on the 3' terminal side of a sense strand of the nucleic acid.

(12) The transformant according to (9), which comprises a nucleic acid encoding a receptor for endocrine disrupting chemicals that interacts with the nucleic acid introduced thereinto.

(13) The transformant according to (12), wherein the receptor for endocrine disrupting chemicals is a juvenile hormone receptor of arthropods.

(14) The transformant according to (13), wherein the juvenile hormone receptor of arthropods is a juvenile hormone receptor of *Crustacea* or an insect.

(15) The transformant according to (14), wherein the juvenile hormone receptor of *Crustacea* is a juvenile hormone receptor of daphnid.

(16) The transformant according to (15), wherein the juvenile hormone receptor of daphnid is a protein (a) or (b):

(a) a protein consisting of the amino acid sequence shown in SEQ ID NO: 12; or (b) a protein consisting of an amino acid sequence having 70% or higher identity to the amino acid sequence shown in SEQ ID NO: 12 and having activity of a transcription factor for a juvenile hormone receptor.

(17) The transformant according to (9), which further comprises a nucleic acid encoding a transcription-coupling factor introduced thereinto.

(18) The transformant according to (9), wherein the host is a yeast.

(19) A method for evaluating a test substance comprising:

a step of bringing a test substance into contact with a transformant comprising the nucleic acid according to any of (1) to (5) and a reporter gene on the 3' terminal side of a sense strand of the nucleic acid introduced into a host and expressing a receptor for endocrine disrupting chemicals that interacts with the nucleic acid; and a step of assaying the expression level of the reporter gene, wherein the interaction between the test substance and the receptor for endocrine disrupting chemicals is evaluated based on the expression level of the reporter gene.

(20) The method of evaluation according to (19), wherein, when the expression level of the reporter gene is increased after the contact with the test substance, the test substance is determined as an agonist for the receptor for endocrine disrupting chemicals.

(21) The method of evaluation according to (19), wherein the test substance is brought into contact with the transformant together with at least one substance selected from the group consisting of the endocrine disrupting chemicals interacting with the receptor for endocrine disrupting chemicals, hormones, and the agonist for the receptor for endocrine disrupting chemicals, and, when the expression level of the reporter gene is lower than the expression level measured when the substance is brought into contact by itself, the test substance is determined as an agonist for the receptor for endocrine disrupting chemicals.

(22) The method of evaluation according to (19), wherein the nucleic acid is designated as a unit and a plurality of units of the nucleic acids are bound to each other.

(23) The method of evaluation according to (19), wherein a nucleic acid encoding the receptor for endocrine disrupting chemicals is introduced into the transformant.

(24) The method of evaluation according to (19), wherein the receptor for endocrine disrupting chemicals is a juvenile hormone receptor of arthropods.

(25) The method of evaluation according to (24), wherein the juvenile hormone receptor of arthropods is a juvenile hormone receptor of *Crustacea* or an insect.

(26) The method of evaluation according to (25), wherein the juvenile hormone receptor of *Crustacea* is a juvenile hormone receptor of daphnid.

(27) The method of evaluation according to (26), wherein the juvenile hormone receptor of daphnid is a protein (a) or (b):

(a) a protein consisting of the amino acid sequence shown in SEQ ID NO: 12; or (b) a protein consisting of an amino acid sequence having 70% or higher identity to the amino acid sequence shown in SEQ ID NO: 12 and having activity of a transcription factor for a juvenile hormone receptor.

(28) The method of evaluation according to (19), wherein the transformant further comprises a nucleic acid encoding a transcription-coupling factor introduced thereinto.

(29) The method of evaluation according to (19), wherein the host is a yeast.

(30) A kit for assaying endocrine disrupting chemicals comprising the vector according to (8) or the transformant according to (11).

Effects of the Invention

The present invention can provide a nucleic acid that is responsive to a small amount of endocrine disrupting chemicals and a vector and a transformant comprising such nucleic acid.

With the use of the nucleic acid according to the present invention, in addition, the reporter gene expression can be analyzed to evaluate the endocrine disrupting actions of the test substance.

EMBODIMENTS OF THE INVENTION

[Response Element]

The nucleic acid according to the present invention (hereafter, it may be referred to as a "response element") comprises a total of 20 to 60 nucleotides comprising the nucleotide sequence shown in SEQ ID NO: 1. The term "response element" used herein does not refer to a sequence as information but the term refers to a nucleic acid comprising 4 nucleotides; i.e., adenine (A), guanine (G), thymine (T), and cytosine (C), bound to each other in a given order. Such response element interacts with a juvenile hormone receptor (an MET protein) of *Daphnia magna* bound to a juvenile hormone and positively regulates the expression of a downstream gene at the transcription level. The nucleotide sequence shown in SEQ ID NO: 1 comprises arbitrary 4 nucleotides (i.e., NNNN) between CACGCG (C-box) and CACGTG (E-box). While such arbitrary 4 nucleotides are not particularly limited, they are preferably kmkk, wherein k indicates G or T and m indicates A or C. Examples of sequences represented by kmkk include 16 types of sequences including GAGG, GCGG, TATT, TCTT, TAGG, TCGG, GATT, GCTT, and so on. Specifically, 4 nucleotides between CACGCG (C-box) and CACGTG (E-box) preferably constitute a sequence selected from among the 16 types of sequences indicated above. It is particularly preferable that 4 nucleotides between CACGCG (C-box) and CACGTG (E-box) be GCGG or TATT. A nucleotide sequence comprising GCGG as arbitrary 4 nucleotides in the nucleotide sequence shown in SEQ ID NO: 1 (i.e., CACGCGGCGGCACGTG) is included in, for example, a promoter sequence located upstream of the Vrille gene of *Daphnia magna*. Nucleotides in a region excluding SEQ ID NO: 1 of a response element can be arbitrarily selected. A full-length of a response element is composed of 20 to 60 nucleotides, preferably 30 to 60 nucleotides, more preferably 40 to 60 nucleotides, and further preferably 40 to 50 nucleotides.

The nucleotide sequence shown in SEQ ID NO: 1 (16 nucleotides) in a response element is preferably located in a region other than the both ends of a full-length sequence of 20 to 60 nucleotides. That is, a response element preferably comprises nucleotide sequences of given nucleotide lengths on the 3' terminal side and the 5' terminal side of the nucleotide sequence shown in SEQ ID NO: 1. A given nucleotide length can be composed of, for example, 1 to 43 nucleotides, preferably 5 to 30 nucleotides, more preferably 5 to 20 nucleotides, and further preferably 7 to 20 nucleotides.

A nucleotide sequence of a region excluding SEQ ID NO: 1 of a response element can be any nucleotide sequence without particular limitation. For example, a nucleotide sequence is preferably selected from a nucleotide sequence adjacent to the nucleotide sequence (i.e., CACGCGGCGGCACGTG) located in an upstream region of the Vrille gene of *Daphnia* magna.

For example, a response element comprising the nucleotide sequence shown in SEQ ID NO: 1 can be a nucleic acid consisting of a nucleotide sequence selected from the group consisting of SEQ ID NOs: 2, 5, 8, 34, and 37. In particular, a response element preferably consists of the nucleotide sequence shown in SEQ ID NO: 2.

The response element according to the present invention can be a nucleotide sequence having 75% or higher, 80% or higher, 85% or higher, 90% or higher, or 95% or higher identity to the nucleotide sequence comprising a region adjacent to the nucleotide sequence (i.e., CACGCGGCGGCACGTG) located in an upstream region of the Vrille gene of *Daphnia magna*. In particular, the nucleotide sequences shown in SEQ ID NO: 40 and SEQ ID NO: 43 comprising 3 nucleotides different from those in SEQ ID NO: 2, the nucleotide sequence shown in SEQ ID NO: 49 comprising 4 nucleotides different from those in SEQ ID NO: 2, the nucleotide sequence shown in SEQ ID NO: 46 comprising 6 nucleotides different from those in SEQ ID NO: 2, and the nucleotide sequence shown in SEQ ID NO: 52 comprising 10 nucleotides different from those in SEQ ID NO: 2 are preferable.

The response element according to the present invention positively regulates the expression of a gene located downstream of the response element (in the 3' direction of a sense strand), independently, at the transcription level. Alternatively, a plurality of response elements may be provided. Specifically, a plurality of a unit of the nucleotide sequence may be provided to be directly adjacent to each other or a plurality of units thereof may be provided via spacers. Thus, a plurality of response elements can be provided upstream of a gene whose expression is regulated at the transcription level.

By providing a plurality of response elements, more potent and positive regulation of downstream gene expression can be induced. While the number of response elements to be provided upstream of a particular gene is not particularly limited, it can be, for example, 2 to 8, preferably 2 to 5, and more preferably 3 to 4.

When a plurality of response elements are to be provided, response elements consisting of nucleotide sequences identical to each other may be provided, response elements consisting of nucleotide sequences different from each other may be provided, or response elements consisting of nucleotide sequences partially identical to each other and different from each other in other regions may be provided.

A spacer to be provided between response elements is not particularly limited, and a spacer can comprise a nucleotide sequence of 1 to a plurality of nucleotides. A nucleotide length of a spacer is not particularly limited, and a spacer can preferably comprise 1 to 100 nucleotides, 1 to 90 nucleotides, 1 to 80 nucleotides, 1 to 70 nucleotides, 1 to 60 nucleotides, 1 to 50 nucleotides, 1 to 40 nucleotides, 1 to 30 nucleotides, 1 to 20 nucleotides, or 1 to 10 nucleotides.

[Vector]

The vector according to the present invention comprises the response element described above. With the aid of the response element, the vector can incorporate a target gene whose expression is to be positively regulated at the transcription level. Specifically, the vector comprises, in a downstream region of the response element, a cloning site into which a target gene whose expression is to be positively regulated at the transcription level is to be incorporated. The vector according to the present invention is not particularly limited, provided that it can regulate downstream gene transcription with the aid of the response element in an adequate host cell. Examples of vectors include a plasmid vector, a phage vector, a cosmid vector, and a donor vector used in genome editing. In addition, a shuttle vector capable of gene exchange between host cells can be used.

Examples of plasmids include *E. coli*-derived plasmid, *Bacillus subtilis*-derived plasmid, and yeast-derived plasmid, and an example of phage is X phage. In addition, animal virus vectors, such as retrovirus, vaccinia virus, or adenovirus vectors, and insect virus vectors, such as baculovirus vectors, can be used.

In order to insert a response element into a vector, at the outset, a purified response element is cleaved with an adequate restriction enzyme, inserted into a restriction enzyme site or a multicloning site of an adequate vector, and ligated to a vector. As a method that does not involve the use of a restriction enzyme, a homologous recombination technique, such as CRISPR/Cas9, Red/ET, or the Gateway method, is adopted.

In the vector according to the present invention, the response element is provided in an expression regulatory region that regulates downstream gene transcription. An expression regulatory region regulates transcription of a downstream gene, and it is generally located upstream of a gene (a 5' region of a sense strand). More specifically, an expression regulatory region can generally be an upstream region of several thousand nucleotides from the transcription initiation site of the downstream gene, and it can be, for example, an upstream region within 5,000 nucleotides (b), preferably 4,000 b, 3,000 b, 2,000 b, 1,000 b, 500 b, or 300 b from the transcription initiation site.

The expression regulatory region may further comprise, in addition to the response element described above, a region to which a transcription factor binds, an enhancer region, and the like. For example, an expression regulatory region comprising the response element described above can be a region of a particular length comprising such response element, such as a 50 b region, a 60 b region, a 70 b region, a 80 b region, a 90 b region, a 100 b region, a 120 b region, a 150 b region, or a 200 b region comprising such response element.

The vector according to the present invention can comprise a gene whose expression is to be regulated in a region downstream of the expression regulatory region comprising the response element constituted as described above. An example of a gene whose expression is to be regulated is a reporter gene. Examples of reporter genes include, but are not particularly limited to, the chloramphenicol acetyltransferase (CAT) gene, the lacZ gene, the luciferase gene, the β-glucuronidase (GUS) gene, the green fluorescent protein (GFP) gene, a drug-resistant gene, and an auxotrophic gene. Reporter genes are not limited to the known genes mentioned above, and the Vrille gene described above may be used as a reporter gene. Specifically, any gene can be used as a reporter gene, provided that the expression level thereof can be monitored at the transcription level.

[Transformant]

The transformant according to the present invention comprises the response element described above introduced into a host. In a transformant, for example, a juvenile hormone receptor of *Daphnia magna* bound to a juvenile hormone interacts with the response element and expression of a gene located downstream of the response element is then enhanced at the transcription level. The response element described above can be introduced into a host with the use of, for example, the vector described above. It is particularly preferable that the transformant according to the present invention comprise the response element described above, a gene whose expression is enhanced by the response element at the transcription level (e.g., a reporter gene), and a nucleic acid encoding a receptor for endocrine disrupting chemicals, such as a juvenile hormone receptor that interreacts with the response element introduced thereinto.

The term "a receptor for endocrine disrupting chemicals" used herein refers to a receptor on which a particular hormone acts as a ligand and a receptor on which an endocrine disrupting chemical having hormone-like action acts. A receptor for endocrine disrupting chemicals encompasses both a cell membrane receptor and an intranuclear receptor. A receptor for endocrine disrupting chemicals preferably interacts with the response element described above and exerts activity of a transcription factor in the presence of a particular hormone or endocrine disrupting chemicals.

Endocrine disrupting chemicals are not particularly limited to, but refer to substances that are known to have endocrine disrupting actions or substances that are suspected of having endocrine disrupting chemicals. Examples of endocrine disrupting chemicals include substances having agonist or antagonist activity on female hormones (follicular hormones (i.e. estrogen) and progestational hormone (i.e. progesterone)) and substances having agonist or antagonist activity on male hormones (androgen). Endocrine disrupting chemicals are not limited to substances having disrupting action on such female or male hormones. Examples thereof include substances having disrupting actions on hormones, such as thyroid hormone, growth hormone, adrenal cortical hormone, or insulin, and neurotransmitters, such as acetylcholine, noradrenalin, adrenalin, or dopamine.

Accordingly, examples of receptors for endocrine disrupting chemicals include receptors for various hormones described above, such as an estrogen receptor, an androgen receptor, a progesterone receptor, a thyroid hormone receptor, a growth hormone receptor, an adrenal cortical hormone receptor, and an insulin receptor.

Examples of endocrine disrupting chemicals include substances having agonist or antagonist activity on arthropod-specific juvenile hormones. Accordingly, it is particularly preferable that a receptor for endocrine disrupting chemicals be a juvenile hormone receptor (MET).

Juvenile hormone receptors are not particularly limited and can be juvenile hormone receptors in arthropods, such as insects, *Crustacea*, Arachnida, and centipede. It is particularly preferable that juvenile hormone receptors in arthropods be juvenile hormone receptors in *Crustacea* or insects.

Examples of insects include *Coleoptera* including beetles and ground beetles, *Lepidoptera* including butterflies and moths, *Diptera* including flies, mosquitos, and gadflies, *Hymenoptera* including bees and ants, Hemiptera including cicadae and shield bugs, Orthoptera including locusts and crickets, and *Odonata* including dragonflies. For the transformant according to the present invention, nucleic acids encoding juvenile hormone receptors derived from such insects can be used.

More specifically, nucleic acids encoding juvenile hormone receptors of *Drosophila melanogaster, Diptera* can be used (He Q et al., J. Biol. Chem., 289 (40), pp. 27874-27885, 2014).

Examples of *Crustacea* include animals of *Crustacea*, including shrimps, crabs, krill, barnacles, and daphnids. For the transformant according to the present invention, nucleic acids encoding juvenile hormone receptors derived from such *Crustacea* can be used.

Among nucleic acids encoding juvenile hormone receptors derived from *Crustacea*, in particular, nucleic acids encoding juvenile hormone receptors derived from animals belonging to Daphniidae are preferably used. Examples of animals belonging to Daphniidae include: animals belonging to *Ceriodaphnia*, such as *Ceriodaphnia cornuta, Ceriodaphnia* reticulata, *Ceriodaphnia dubia, Ceriodaphnia* megalops, *Ceriodaphnia pulchella*, and *Ceriodaphnia* quadrangular; animals belonging to *Daphnia*, such as *Daphnia* similis, *Daphnia* magna, *Daphnia* pulex, *Daphnia* pulicaria, *Daphnia* ambigua, *Daphnia* obtuse, *Daphnia* biwaensis, *Daphnia* longispina, *Daphnia* rosea, *Daphnia* hyaline, *Daphnia* galeata, *Daphnia* ezoensis, *Daphnia* cuculata, *Daphnia cristata*, and *Daphnia longiremis*; animals belonging to *Scapholeberis*, such as *Scapholeberis mucronate* and *Scapholeberis kingi*; and animals belonging to *Simocephalus*, such as *Simocephalus serrulatus, Simocephalus exspinosus, Simocephalus vetulus, Simocephalus vetuloides*, and *Simocephalus japonica*.

Among them, in particular, nucleic acids encoding juvenile hormone receptors derived from animals belonging to *Daphnia* are preferably used, and nucleic acids encoding juvenile hormone receptors derived from *Daphnia magna* are more preferably used. The amino acid sequence of the juvenile hormone receptor derived from *Daphnia magna* is shown in SEQ ID NO: 12, and the nucleotide sequence of a nucleic acid encoding the juvenile hormone receptor is shown in SEQ ID NO: 11.

It should be noted that the transformant according to the present invention is not limited to a transformant comprising a nucleic acid encoding a juvenile hormone receptor consisting of the amino acid sequence shown in SEQ ID NO: 12, and the transformant may comprise a nucleic acid encoding a protein comprising an amino acid sequence having 70% or higher, preferably 80% or higher, more preferably 90% or higher, further preferably 95% or higher, and most preferably 98% or higher identity to the amino acid sequence shown in SEQ ID NO: 12 and having activity of a transcription factor for a juvenile hormone receptor.

The identity between amino acid sequences can be determined using the BLASTN or BLASTX program equipped with the Basic Local Alignment Search Tool (BLAST) algorithm (default settings). The identity is determined by subjecting a pair of amino acid sequences to pair-wise alignment analysis, calculating the number of amino acid residues completely identical between the amino acid sequences, and determining the percentage of the completely identical amino acid residues in all the amino acid residues subjected to comparison.

It should also be noted that the transformant according to the present invention is not limited to a transformant comprising a nucleic acid encoding a juvenile hormone receptor consisting of the amino acid sequence shown in SEQ ID NO: 12, and the transformant may comprise a nucleic acid encoding a protein that is encoded by a nucleic acid hybridizing under stringent conditions to a part or a full-length of a complementary strand of the nucleic acid consisting of the nucleotide sequence shown in SEQ ID NO: 11 and has activity of a transcription factor for a juvenile hormone receptor. Under "stringent conditions," a so-called specific hybrid is formed, but a non-specific hybrid is not formed. Stringent conditions can be adequately determined with reference to, for example, Molecular Cloning: A Laboratory Manual (Third Edition). Specifically, an extent of stringency can be determined by adjusting temperature and salt concentration in a solution at the time of Southern hybridization and temperature and salt concentration in a solution in the step of washing in Southern hybridization. Under stringent conditions, more specifically, sodium concentration is 25 to 500 mM and preferably 25 to 300 mM, and temperature is 42° C. to 68° C. and preferably 42° C. to 65° C. Further specifically, sodium concentration is 5×SSC (83 mM NaCl, 83 mM sodium citrate), and temperature is 42° C.

Whether or not a protein encoded by a nucleic acid consisting of a particular nucleotide sequence other than the sequence shown in SEQ ID NO: 11 or whether or not a protein comprising amino acids different from those shown in SEQ ID NO: 12 has activity of a transcription factor for a juvenile hormone receptor can be evaluated in the manner described below. Specifically, a transformant comprising a target nucleic acid to be evaluated or a nucleic acid encoding a target protein to be evaluated, the response element described above, and a reporter gene downstream thereof introduced therein is first prepared. The transformant is then cultured in the presence or absence of juvenile hormones, and expression of the reporter gene is measured. When the expression level of the reporter gene in the presence of juvenile hormones is significantly higher than the expression level of the reporter gene in the absence of juvenile hormones, the target nucleic acid to be evaluated is determined to encode a protein having activity of a transcription factor for a juvenile hormone receptor and the target protein to be evaluated is determined to have activity of a transcription factor for a juvenile hormone receptor.

Thus, the activity of a transcription factor for a juvenile hormone receptor described above can also be referred to as activity for interacting with the response element according to the present invention. Further, the activity of a transcription factor for a juvenile hormone receptor described above can also be referred to as activity for binding to juvenile hormones and interacting with the response element according to the present invention.

In addition to the nucleic acid, the response element, and the reporter gene, the transformant according to the present invention may comprise a nucleic acid encoding a transcription-coupling factor. Examples of transcription-coupling factors include, but are not particularly limited to, Taiman (Tai), the steroid receptor coactivator (SRC), β-FTZ-F1 (fushi tarazu binding factor 1), the interacting steroid receptor coactivator (FISC), the CREB binding protein (CBP), P300, the transcriptional mediators/intermediary factor 2 (TIF2), amplified in breast cancer (AIB), the 70 kDa androgen receptor coactivator (ARA70), the activating signal co-integrator 2 (ASC2), and the 140 kDa estrogen receptor-associated protein (ERAP140). By introducing nucleic acids encoding such transcription-coupling factors, activity of a receptor for endocrine disrupting chemicals to accelerate transcription of the reporter gene can be activated.

Introduction of a nucleic acid encoding SRC or Tai is particularly preferable, and introduction of a nucleic acid encoding SRC of *Daphnia magna* is more preferable. SEQ ID NO: 14 shows the amino acid sequence of SRC of

*Daphnia magna* and SEQ ID NO: 13 shows the nucleotide sequence of a nucleic acid encoding such SRC.

It should be noted that a transcription-coupling factor that can be used for the transformant according to the present invention is not limited to the protein consisting of the amino acid sequence shown in SEQ ID NO: 14, and a transcription-coupling factor may be a protein comprising an amino acid sequence having 70% or higher, preferably 80% or higher, more preferably 90% or higher, further preferably 95% or higher, and most preferably 98% or higher identity to the amino acid sequence shown in SEQ ID NO: 14 and having activity of the transcription-coupling factor.

A host of the transformant according to the present invention can be *E. coli, Bacillus subtilis*, budding yeast, an arthropod- or mammal-derived cultured cell, an undifferentiated plant cell (*callus*), nematode (*C. elegans*), arthropods such as daphnids or *Drosophila*, fish such as zebrafish or *Oryzias latipes*, amphibian such as *Xenopus laevis* or newt, a mammal such as a mouse or rat, or a higher plant such as *Arabidopsis thaliana* or *Oryza sativa*, with budding yeast being preferable. The above described nucleic acid or the response element, the reporter gene, the vector, and the like can be introduced into a host by any known method without particular limitation. Examples of methods for nucleic acid introduction include the lithium acetate method, the calcium phosphate method, a method involving the use of a liposome, electroporation, a method involving the use of a viral vector, and the micropipette injection method. Introduction of the above described nucleic acid or the response element, the reporter gene, and the like into the transformant according to the present invention may be transient, provided that it can be used for analysis. The above described nucleic acid or the response element, the reporter gene, the vector, and the like may be integrated into a host chromosome and introduced into the transformant. Alternatively, the above described nucleic acid or the response element, the reporter gene, the vector, and the like may be introduced into the transformant with the aid of an artificial chromosome or plasmid capable of autonomous replication and division.

In the transformant according to the present invention constituted as described above, a receptor for endocrine disrupting chemicals to which a particular hormone or endocrine disrupting chemical has bound interacts with a response element, and expression of a gene (e.g., a reporter gene) located downstream of the response element is then enhanced at the transcription level. By measuring the expression of a gene located downstream of the response element, accordingly, the interaction between the receptor for endocrine disrupting chemicals and the response element can be evaluated. On the basis of such phenomenon, the influence of a particular substance (a test substance) on the interaction between the receptor for endocrine disrupting chemicals and the response element can be evaluated. More specifically, the ability of a test substance for binding to a receptor for endocrine disrupting chemicals or the influence of a test substance on the binding between a receptor for endocrine disrupting chemicals and its agonist can be evaluated on the basis of the expression of the gene located downstream of the response element. The transformant according to the present invention involves the use of the response element described above. Thus, whether or not the test substance has endocrine disrupting actions other than the particular endocrine disrupting actions can be evaluated.

A test substance is not particularly limited, and any substance can serve as a test substance. Examples of test substances include a low-molecular-weight compound, a high-molecular-weight compound, a peptide, a single compound, a composition comprising a plurality of compounds, a culture product, an extract, a naturally-occurring substance, and a synthetic compound.

Specifically, a transformant is cultured in the presence or absence of a test substance, and the expression of a reporter gene located downstream of the response element in the presence of a test substance and that in the absence of a test substance are measured. When the expression level of the reporter gene in the presence of the test substance is significantly higher than that in the absence of the test substance, the test substance can be determined to interact with a receptor for endocrine disrupting chemicals and have agonist action to positively regulate the gene expression through the response element described above. In such a case, specifically, it is highly likely that the test substance is an endocrine disrupting chemical having agonist activity.

Alternatively, a transformant is cultured in the presence or absence of a test substance and a substance having agonist action on a receptor for endocrine disrupting chemicals, and the expression of a reporter gene located downstream of the response element in the presence of these substances and that in the absence of thee substance are measured. When the expression level of the reporter gene in the presence of the test substance is significantly lower than that in the absence of the test substance, the test substance can be determined to inhibit agonist action on a receptor for endocrine disrupting chemicals and have antagonist activity to negatively regulate the gene expression through the response element described above. In such a case, specifically, it is highly likely that the test substance is an endocrine disrupting chemical having antagonist activity. A substance exerting agonist action on a receptor for endocrine disrupting chemicals is a substance selected from among a hormone that acts on a receptor for endocrine disrupting chemicals, endocrine disrupting chemicals to such hormone, and an agonist compound of a receptor for endocrine disrupting chemicals.

With the use of the transformant according to the present invention, as described above, endocrine disrupting actions of the test substance can be evaluated via a very simple procedure. Specifically, the transformant according to the present invention can be used for measurement and evaluation of endocrine disrupting chemicals and a kit for measurement of endocrine disrupting chemicals for evaluation of endocrine disrupting actions of the test substance can be prepared.

When a transformant comprising a nucleic acid encoding a juvenile hormone receptor of *Daphnia magna* as a receptor for endocrine disrupting chemicals, the response element described above, and a reporter gene introduced thereinto is used, endocrine disrupting actions of the test substance on animals of Daphniidae, in particular, *Daphnia magna*, can be evaluated with high reliability.

When a yeast host is used, the transformant according to the present invention eliminates the influence, such as degradation of a test substance caused by a P450 or other drug metabolizing system of an animal cell, and enables accurate evaluation of endocrine disrupting actions of the test substance.

EXAMPLES

Hereafter, the present invention is described in greater detail with reference to the examples, although the technical scope of the present invention is not limited to the following examples.

[Preparation of Yeast Transformant]

In the examples, reporter plasmids, plasmids for transcription factors (receptors for endocrine disrupting chemicals), and plasmids for transcription-coupling factors were prepared as described below and introduced into budding yeast strains to prepare yeast transformants.

[Preparation of Reporter Plasmids]

Oligo DNA (SEQ ID NO: 3) comprising a response element consisting of the nucleotide sequence shown in SEQ ID NO: 2 (43 nucleotides) and oligo DNA (SEQ ID NO: 4) partially complementary to SEQ ID NO: 3 were prepared and annealed to each other. At the time of annealing, oligo DNAs were incubated at 95° C. for 2 minutes and temperature was then gradually lowered from 90° C. to 37° C. over the time of 30 minutes. When two sequences are "partially complementary" to each other herein, a region excluding several nucleotides on the 5' terminal side of a nucleotide sequence identified by a sequence identification number is complementary to the same region of the other sequence.

After annealing, oligo DNA in which 1, 2, 3, 4, or 5 response elements had been consecutively annealed was purified. Subsequently, oligo DNA resulting from consecutive annealing of 1, 2, 3, 4, or 5 response elements shown in SEQ ID NO: 2 was inserted into the SpeI site of the pRW95-3 μlasmid having the β-galactosidase gene prepared in accordance with the method described in Wolf S S et al., Biotechniques, 20 (4), pp. 568-573, 1996.

Plasmids each comprising the response element (54 nucleotides) consisting of the nucleotide sequence shown in SEQ ID NO: 5, the response element (30 nucleotides) consisting of the nucleotide sequence shown in SEQ ID NO: 8, the response element (22 nucleotides) consisting of the nucleotide sequence shown in SEQ ID NO: 34, the response element (36 nucleotides) consisting of the nucleotide sequence shown in SEQ ID NO: 37, the response element (43 nucleotides) consisting of the nucleotide sequence shown in SEQ ID NO: 40, the response element (43 nucleotides) consisting of the nucleotide sequence shown in SEQ ID NO: 43, the response element (43 nucleotides) consisting of the nucleotide sequence shown in SEQ ID NO: 46, the response element (43 nucleotides) consisting of the nucleotide sequence shown in SEQ ID NO: 49, or the response element (43 nucleotides) consisting of the nucleotide sequence shown in SEQ ID NO: 52 inserted thereinto were prepared in the same manner. Plasmids were prepared in the same manner except that oligo DNA shown in SEQ ID NO: 6, SEQ ID NO: 9, SEQ ID NO: 35, SEQ ID NO: 38, SEQ ID NO: 41, SEQ ID NO: 44, SEQ ID NO: 47, SEQ ID NO: 50, or SEQ ID NO: 53 was used instead of the oligo DNA shown in SEQ ID NO: 3, and oligo DNA partially complementary to SEQ ID NO: 6 (SEQ ID NO: 7), oligo DNA partially complementary to SEQ ID NO: 9 (SEQ ID NO: 10), oligo DNA partially complementary to SEQ ID NO: 35 (SEQ ID NO: 36), oligo DNA partially complementary to SEQ ID NO: 38 (SEQ ID NO: 39), oligo DNA partially complementary to SEQ ID NO: 41 (SEQ ID NO: 42), oligo DNA partially complementary to SEQ ID NO: 44 (SEQ ID NO: 45), oligo DNA partially complementary to SEQ ID NO: 47 (SEQ ID NO: 48), oligo DNA partially complementary to SEQ ID NO: 50 (SEQ ID NO: 51), or oligo DNA partially complementary to SEQ ID NO: 53 (SEQ ID NO: 54) was used instead of the oligo DNA shown in SEQ ID NO: 4. Thus, a plasmid comprising 3 consecutive repeats of the response element shown in SEQ ID NO: 5 inserted thereinto, a plasmid comprising 1, 2, 3, or 4 consecutive repeats of the response element shown in SEQ ID NO: 8 inserted thereinto, a plasmid comprising 1, 2, 3, 4, or 5 consecutive repeats of the response element shown in SEQ ID NO: 34 inserted thereinto, a plasmid comprising 1, 2, 3, or 4 consecutive repeats of the response element shown in SEQ ID NO: 37 inserted thereinto, a plasmid comprising 1, 2, 3, or 4 consecutive repeats of the response element shown in SEQ ID NO: 40 inserted thereinto, a plasmid comprising 1, 2, 3, or 4 consecutive repeats of the response element shown in SEQ ID NO: 43 inserted thereinto, a plasmid comprising 1, 2, or 3 consecutive repeats of the response element shown in SEQ ID NO: 46 inserted thereinto, a plasmid comprising 1, 2, 3, or 4 consecutive repeats of the response element shown in SEQ ID NO: 49 inserted thereinto, and a plasmid comprising 1, 2, or 3 consecutive repeats of the response element shown in SEQ ID NO: 52 inserted thereinto were prepared. The nucleotide sequences shown in SEQ ID NO: 2, SEQ ID NO: 5, SEQ ID NO: 8, SEQ ID NO: 34, and SEQ ID NO: 37 are located upstream of the Vrille gene of *Daphnia magna*, the nucleotide sequence shown in SEQ ID NO: 40 is derived from the nucleotide sequence shown in SEQ ID NO: 2 by substitution of 3 nucleotides outside the 5' terminus of the C-box (CACGCG), the nucleotide sequence shown in SEQ ID NO: 43 is derived from the nucleotide sequence shown in SEQ ID NO: 2 by substitution of 3 nucleotides outside the 3' terminus of the E-box (CACGTG), the nucleotide sequence shown in SEQ ID NO: 46 is derived from the nucleotide sequence shown in SEQ ID NO: 2 by substitution of 3 nucleotides outside the 5' terminus of the C-box (CACGCG) and 3 nucleotides outside the 3' terminus of the E-box (CACGTG), the nucleotide sequence shown in SEQ ID NO: 49 is derived from the nucleotide sequence shown in SEQ ID NO: 2 by substitution of 4 nucleotides in a region (a linker region) between the C-box (CACGCG) and the E-box (CACGTG), and the nucleotide sequence shown in SEQ ID NO: 52 is derived from the nucleotide sequence shown in SEQ ID NO: 2 by substitution of 3 nucleotides outside the 5' terminus of the C-box (CACGCG), 3 nucleotides outside the 3' terminus of the E-box (CACGTG), and 4 nucleotides in a region (a linker region) between the C-box (CACGCG) and the E-box (CACGTG).

For comparison with the reporter plasmid comprising the response element, a plasmid comprising the nucleic acid consisting of 16 nucleotides (i.e., CACGCGGCGGCACGTG) located in an upstream region of the Vrille gene of *Daphnia magna* inserted thereinto was prepared. Such 16 nucleotides include the E-box (CACGTG) and the C-box (CACGCG) serving as juvenile hormone response elements in various insects. In accordance with the method for preparing plasmids described above, a plasmid comprising 1, 2, 3, or 4 consecutive repeats of the nucleic acid consisting of 16 nucleotides inserted thereinto was prepared.

For further comparison, a plasmid comprising a region including the juvenile hormone response element of the Kr-hi gene of *Drosophila melanogaster* (DmJHRR) inserted thereinto was prepared. DmJHRR is described in He Q et al., J. Biol. Chem., 289 (40), pp. 27874-27885, 2014. A plasmid comprising 3 consecutive repeats of the DmJHRR sequence inserted thereinto was prepared in accordance with the method described above, except that oligo DNA comprising the DmJHRR sequence (SEQ ID NO: 15) was used instead of the oligo DNA shown in SEQ ID NO: 3 and oligo DNA partially complementary to SEQ ID NO: 15 (SEQ ID NO: 16) was used instead of the oligo DNA shown in SEQ ID NO: 4.

In order to compare reporter activity influenced by the presence or absence of the C-box (CACGCG) and the E-box (CACGTG) in the nucleotide sequence shown in SEQ ID NO: 2, a nucleotide sequence having a C-box different from the C-box in SEQ ID NO: 2 (SEQ ID NO: 25), a nucleotide sequence having an E-box different from the E-box in SEQ ID NO: 2 (SEQ ID NO: 28), and a nucleotide sequence having a C-box and an E-box different from the C-box and the E-box in SEQ ID NO: 2 (SEQ ID NO: 31) were prepared. Specifically, oligo DNA comprising the nucleotide sequence shown in SEQ ID NO: 25 (SEQ ID NO: 26) and DNA partially complementary to SEQ ID NO: 26 (SEQ ID NO: 27), oligo DNA comprising the nucleotide sequence shown in SEQ ID NO: 28 (SEQ ID NO: 29) and DNA partially complementary to SEQ ID NO: 29 (SEQ ID NO: 30), and oligo DNA comprising the nucleotide sequence shown in SEQ ID NO: 31 (SEQ ID NO: 32) and DNA partially complementary to SEQ ID NO: 32 (SEQ ID NO: 33) were prepared, and a plasmid comprising 4 consecutive repeats of the nucleotide sequence shown in SEQ ID NO: 25 inserted thereinto, a plasmid comprising 4 consecutive repeats of the nucleotide sequence shown in SEQ ID NO: 28 inserted thereinto, and a plasmid comprising 4 consecutive repeats of the nucleotide sequence shown in SEQ ID NO: 31 inserted thereinto were prepared.

[Preparation of a Plasmid Expressing a Transcription Factor]

In order to prepare a plasmid expressing a juvenile hormone receptor of *Daphnia magna* (hereafter, referred to as a “DampaMET plasmid”), a CEN6/ARS4 fragment was first prepared. A DNA fragment comprising the autonomously replicating sequence (ARS) and the centromere sequence (CEN) of yeast was amplified by PCR with the use of, as a template, the pYTβ reporter plasmid and the primers for CEN/ARS amplification: pUdp6 I-SceI CEN6 FW (SEQ ID NO: 17) and pUdp6 I-SceI ARS4 RE (SEQ ID NO: 18). PCR was carried out by repeating a cycle of 94° C. for 20 seconds, 58° C. for 20 seconds, and 72° C. for 1.5 minutes 35 times.

A PCR-amplified fragment and the pUdp6 μlasmid linearized by cleavage with the AatII restriction enzyme were introduced into wild-type yeast strains (*Saccharomyces cerevisiae*) W303a (MATa, ade2, his3, leu2, trpl, ura3) by the lithium acetate method. The pUdp6 μlasmid has a bidirectional promoter regions gal1 and gal10, a CYC terminator downstream of gal10, an ADH terminator downstream of gal1, and the uracil selection marker URA3 gene. A plasmid comprising the CEN6/ARS4 fragment inserted into pUdp6 via homologous recombination was extracted from yeast and introduced into the *E. coli* DH5α strain to prepare a low-copy episomal vector pUdp13. A recognition sequence of the 18-bp I-SceI restriction enzyme has been introduced into a site outside the CEN6/ARS4 sequence. After the target gene is cloned into the multicloning site, accordingly, the CEN6/ARS4 fragment is cleaved with I-SceI, and the resulting fragment can be readily converted into a genome insertion-type plasmid.

Subsequently, an open reading frame (ORF) of cDNA of the DampaMET gene was amplified by PCR using, as a template, cDNA of adult *Daphnia magna* carrying a resting egg and the primers for DampaMET: MET FW2 (SEQ ID NO: 19) and MET REV-3 (SEQ ID NO: 20). PCR was carried out by repeating a cycle of 94° C. for 20 seconds, 58° C. for 20 seconds, and 72° C. for 2.5 minutes 35 times.

cDNA of the amplified DampaMET gene and the pUdp13 μlasmid cleaved with the BamHI and HindIII restriction enzymes were introduced into the wild-type yeast strain W303a by the lithium acetate method. A plasmid prepared by this method, which comprises cDNA of the DampaMET gene inserted into a site downstream of the GAL10 promoter of the pUdp13 plasmid, was designated as pUdp13-DapmaMet. pUdp13-DapmaMet constructed in a yeast cell was recovered, introduced into the *E. coli* DH5a strain, and amplified.

Subsequently, pUdp13-DapmaMet was cleaved with the I-SceI restriction enzyme to obtain the CEN6/ARS4 sequence and converted into a genome insertion-type plasmid. Thus, the DampaMET plasmid comprising the DampaMET gene and a promoter upstream thereof was obtained.

A plasmid expressing a juvenile hormone receptor of *Drosophila melanogaster* (hereafter, referred to as a “DmMET plasmid”) was prepared in the same manner. At the outset, ORF of cDNA of the DmMET gene was amplified by PCR using, as a template, cDNA of *Drosophila melanogaster* larvae (Clontech) and the primers for DmMET: DmMET Fwd (SEQ ID NO: 21) and DmMET Rev (SEQ ID NO: 22). PCR was carried out by repeating a cycle of 98° C. for 10 seconds, 55° C. for 30 seconds, and 68° C. for 1.5 minutes 25 times.

cDNA of the amplified DmMET gene was cleaved with the SmaI and EcoRI restriction enzymes. cDNA of the cleaved DmMET gene was inserted into a region downstream of the GAL10 promoter of the pUdp6 μlasmid cleaved with the SmaI and EcoRI restriction enzymes. Thus, the DmMET plasmid comprising the DmMET gene and a promoter upstream thereof was obtained.

[Preparation of a Plasmid Expressing a Transcription-Coupling Factor]

In the example, in particular, a plasmid expressing a transcription factor comprising the *Drosophila melanogaster* Tai (DmTai) gene (hereafter, referred to as a “DmTai plasmid”) and a plasmid expressing a *Daphnia magna* transcription-coupling factor (SRC) (hereafter, referred to as a “DampaSRC plasmid”) were prepared and used. The DmTai plasmid was prepared in accordance with Ito-Harashima S et al., FEBS Open Bio., 7 (7): pp. 995-1008, 2017.

The DampaSRC plasmid was prepared in the manner described below. At the outset, ORF of cDNA of the *Daphnia magna* SRC (DampaSRC) gene was amplified by PCR using, as a template, cDNA of adult *Daphnia magna* carrying a resting egg and the primers for SRC: SRC-F1F-pESC (SEQ ID NO: 23) and SRC-F4short-pESC (SEQ ID NO: 24). PCR was carried out by repeating a cycle of 94° C. for 20 seconds, 58° C. for 10 seconds, and 72° C. for 7 minutes 35 times.

Subsequently, the pESC-Leu plasmid (Agilent technology) was cleaved with the SpeI and PacI restriction enzymes, and cDNA of the amplified DampaSRC gene was introduced into the wild-type yeast strain W303a by the lithium acetate method. Thus, the DampaSRC plasmid comprising cDNA of the DampaSRC gene inserted downstream of the gal1 promoter region of the pESC-Leu plasmid was obtained. The DampaSRC plasmid constructed in a yeast cell was recovered, introduced into the *E. coli* DH5a strain, and amplified.

[Preparation of Yeast Transformant]

At the outset, the cells of the budding yeast strain W303a were cultured in a YPD medium (1% yeast extract, 2% peptone, 2% D (+)-glucose) at 30° C. until the turbidity (O.D. 595) reached 0.7 to 0.8. The cultured cells were washed 2 times with sterile water and resuspended in a 0.1 mol/1 lithium acetate solution in an amount of 1/10 of the culture solution using a pipette. The cell suspension was fractionated in an amount of 100 μl each to 1.5-ml microtubes, and the supernatant was removed via centrifugation. A TE buffer (75 μl; 10 mM Tris, 1 mM EDTA, pH 8.0) containing 1 μg of the DampaMET plasmid linearized via treatment with the EcoRV restriction enzyme and 50 μg of carrier DNA (tradename: SALMON TESTESDNA for hybridization, SIGMA) was added, and 240 μl of a 50% polyethylene glycol 3350 solution and 36 μl of a 0.1 mol/1 lithium acetate solution were further added, followed by thorough mixing.

The mixture was incubated at 30° C. for 30 minutes, heat-treated at 42° C. for 22 minutes, and centrifuged at 9,000 rpm for 1 minute to harvest yeast cells from the mixture. The harvested yeast cells were suspended in 300 μl of sterile water, 100 ml of the suspension was applied to a selection medium prepared by adding 42 mg of tryptophan, 62 mg of leucine, and 2% agarose to the medium shown in Table 1 and Table 2, and culture was then performed. Uracil-nonrequiring yeast strains were selected as yeast transformants comprising the gal1 promoter and the cDNA region of the MET gene integrated into the chromosome.

Subsequently, the DampaSRC plasmid was introduced into the yeast transformant comprising the DampaMET plasmid introduced thereinto. As a selection medium for the yeast transformant, a culture medium prepared by adding 100 mg of tryptophan to the culture medium shown in Table 1 and Table 2 was used.

TABLE 1

| Composition of pre-culture medium | |
|---|---|
| Components | Amount |
| Yeast nitrogen base w/o amino acids and ammonium sulfate | 1.7 g |
| $(NH_4)_2SO_4$ | 5 g |
| Drop-out powder (Table 2) | 1.3 g |
| 5M NaOH | 500 μl |

TABLE 1-continued

| Composition of pre-culture medium | |
|---|---|
| Components | Amount |
| D(+)-glucose | 20 g |
| Water | 11 |

Solid medium was prepared with the addition of 2% agar to the above composition, autoclaving, and transfer to a petri dish

TABLE 2

| Composition of drop-out powder | |
|---|---|
| Components | Amount |
| Adenine | 2.5 g |
| L-Aspartic acid | 6.0 g |
| L-Histidine | 1.2 g |
| L-Arginine-HCl | 1.2 g |
| L-Methionine | 1.2 g |
| L-Lysine-HCl | 1.8 g |
| L-Glutamic acid | 6.0 g |
| L-Valine | 9.0 g |
| L-Serine | 22.5 g |
| L-Threonine | 12.0 g |

Subsequently, a reporter plasmid prepared by inserting the nucleotide sequence shown in SEQ ID NO: 2 into a yeast comprising the DampaMET plasmid and the DampaSRC plasmid introduced thereinto by the lithium acetate method. As a selection medium, the pre-culture medium shown in Table 1 and Table 2 was used. Thus, Yeast 1 of Invention was obtained. In the same manner, Yeasts 2 to 38 of Invention each comprising the response element according to the present invention and Control yeasts 1 to 9 shown in Table 3 were prepared.

TABLE 3

| | Response element type | Response element unit | Transcription factor | Coupling factor |
|---|---|---|---|---|
| Yeast 1 of Invention | SEQ ID NO: 2 | 1 | DampaMET | DampaSRC |
| Yeast 2 of Invention | SEQ ID NO: 2 | 2 | DampaMET | DampaSRC |
| Yeast 3 of Invention | SEQ ID NO: 2 | 3 | DampaMET | DampaSRC |
| Yeast 4 of Invention | SEQ ID NO: 2 | 4 | DampaMET | DampaSRC |
| Yeast 5 of Invention | SEQ ID NO: 2 | 5 | DampaMET | DampaSRC |
| Yeast 6 of Invention | SEQ ID NO: 5 | 3 | DampaMET | DampaSRC |
| Yeast 7 of Invention | SEQ ID NO: 8 | 3 | DampaMET | DampaSRC |
| Yeast 8 of Invention | SEQ ID NO: 2 | 4 | DmMET | DmTai |
| Yeast 9 of Invention | SEQ ID NO: 34 | 1 | DampaMET | DampaSRC |
| Yeast 10 of Invention | SEQ ID NO: 34 | 2 | DampaMET | DampaSRC |
| Yeast 11 of Invention | SEQ ID NO: 34 | 3 | DampaMET | DampaSRC |
| Yeast 12 of Invention | SEQ ID NO: 34 | 4 | DampaMET | DampaSRC |
| Yeast 13 of Invention | SEQ ID NO: 34 | 5 | DampaMET | DampaSRC |
| Yeast 14 of Invention | SEQ ID NO: 8 | 1 | DampaMET | DampaSRC |
| Yeast 15 of Invention | SEQ ID NO: 8 | 2 | DampaMET | DampaSRC |
| Yeast 16 of Invention | SEQ ID NO: 8 | 4 | DampaMET | DampaSRC |
| Yeast 17 of Invention | SEQ ID NO: 37 | 1 | DampaMET | DampaSRC |
| Yeast 18 of Invention | SEQ ID NO: 37 | 2 | DampaMET | DampaSRC |
| Yeast 19 of Invention | SEQ ID NO: 37 | 3 | DampaMET | DampaSRC |
| Yeast 20 of Invention | SEQ ID NO: 37 | 4 | DampaMET | DampaSRC |
| Yeast 21 of Invention | SEQ ID NO: 40 | 1 | DampaMET | DampaSRC |
| Yeast 22 of Invention | SEQ ID NO: 40 | 2 | DampaMET | DampaSRC |
| Yeast 23 of Invention | SEQ ID NO: 40 | 3 | DampaMET | DampaSRC |
| Yeast 24 of Invention | SEQ ID NO: 40 | 4 | DampaMET | DampaSRC |
| Yeast 25 of Invention | SEQ ID NO: 43 | 1 | DampaMET | DampaSRC |
| Yeast 26 of Invention | SEQ ID NO: 43 | 2 | DampaMET | DampaSRC |
| Yeast 27 of Invention | SEQ ID NO: 43 | 3 | DampaMET | DampaSRC |
| Yeast 28 of Invention | SEQ ID NO: 43 | 4 | DampaMET | DampaSRC |
| Yeast 29 of Invention | SEQ ID NO: 46 | 1 | DampaMET | DampaSRC |
| Yeast 30 of Invention | SEQ ID NO: 46 | 2 | DampaMET | DampaSRC |
| Yeast 31 of Invention | SEQ ID NO: 46 | 3 | DampaMET | DampaSRC |

TABLE 3-continued

| | Response element type | Response element unit | Transcription factor | Coupling factor |
|---|---|---|---|---|
| Yeast 32 of Invention | SEQ ID NO: 49 | 1 | DampaMET | DampaSRC |
| Yeast 33 of Invention | SEQ ID NO: 49 | 2 | DampaMET | DampaSRC |
| Yeast 34 of Invention | SEQ ID NO: 49 | 3 | DampaMET | DampaSRC |
| Yeast 35 of Invention | SEQ ID NO: 49 | 4 | DampaMET | DampaSRC |
| Yeast 36 of Invention | SEQ ID NO: 52 | 1 | DampaMET | DampaSRC |
| Yeast 37 of Invention | SEQ ID NO: 52 | 2 | DampaMET | DampaSRC |
| Yeast 38 of Invention | SEQ ID NO: 52 | 3 | DampaMET | DampaSRC |
| Control yeast 1 | cacgcggcggcacgtg | 1 | DampaMET | DampaSRC |
| Control yeast 2 | cacgcggcggcacgtg | 2 | DampaMET | DampaSRC |
| Control yeast 3 | cacgcggcggcacgtg | 3 | DampaMET | DampaSRC |
| Control yeast 4 | cacgcggcggcacgtg | 4 | DampaMET | DampaSRC |
| Control yeast 5 | DmJHRR | 3 | DampaMET | DmTai |
| Control yeast 6 | DmJHRR | 3 | DmMET | DmTai |
| Control yeast 7 | SEQ ID NO: 25 | 4 | DampaMET | DampaSRC |
| Control yeast 8 | SEQ ID NO: 28 | 4 | DampaMET | DampaSRC |
| Control yeast 9 | SEQ ID NO: 31 | 4 | DampaMET | DampaSRC |

The test examples described below were performed using the yeast transformants.

[Test Example 1] Assay of Reporter Activity of Yeast Transformant to Juvenile Hormones With the use of the Yeast 1 of Invention, reporter activity to methyl farnesoate as a juvenile hormone substance was measured. At the outset, the Yeast 1 of Invention was subjected to pre-culture at 30° C. for 18 hours using the pre-culture medium shown in Table 1 until the turbidity (O.D. 595) of the pre-culture medium reached approximately 0.1. The solution of the pre-cultured cells (10 µl) and 1 µl of the solution of methyl farnesoate diluted to various concentrations with dimethyl sulfoxide (DMSO) were mixed with 90 µl of the main culture solution shown in Table 4 in a 96-well plate, and the mixture was subjected to static culture at 30° C. for 18 hours to prepare a reaction solution. The resultant was designated as a test group.

TABLE 4

| Composition of main culture medium | |
|---|---|
| Components | Amount |
| Yeast nitrogen base w/o amino acids and ammonium sulfate | 1.7 g |
| $(NH_4)_2SO_4$ | 5.0 g |
| Drop-out powder (Table 2) | 1.3 g |
| 5M NaOH | 500 µl |
| D(+)-galactose | 10 g |
| Water | 1l |

A reaction solution prepared with the addition of 1 µl of DMSO instead of a diluted methyl farnesoate solution was designated as a control group. Fractions of 10 µl each were collected from the reaction solutions and dispensed into each well of another 96-well plate. Thereafter, 100 µl of an assay reagent comprising a lytic solution (Z buffer: 60 mM $Na_2HPO_4$, 40 mM $NaH_2PO_4$, 1 mM $MgCl_2$, 10 mM KCl, 2 mM dithiothreitol, 0.20% N-lauroylsarcosine sodium salt) mixed with 1 mg/ml ONPG (orthonitrophenylgalactopyranoside) was dispensed into each well, and the reaction was allowed to proceed at 37° C. for 30 minutes. Thereafter, the absorbance (O.D. 405) and the turbidity (O.D. 595) of the reaction solutions were assayed at the wavelength of 405 nm using a microplate reader (tradename: iMark microplate reader, Bio-Rad Laboratories). The increase of induction was calculated in accordance with the following formula.

$$\text{Increase in induction} = \frac{O.D.405\text{ of Test group}}{O.D.595\text{ of Test group}} - \frac{O.D.405\text{ of Control group}}{O.D.595\text{ of Control group}}$$

The increase of induction is described in Ito-Harashima S et al., FEBS Open Bio., 7 (7): pp. 995-1008, 2017. When the increase of induction is positive, the transformant is determined to have reporter activity to the substance tested. The test was performed once or repeated 3 times, 5 times, or 15 times, and the average increase of induction was calculated. The control yeast 1 was treated in the same manner and reporter activity was compared. The results are shown in Table 5.

TABLE 5

| Tested yeast transformant | Amount of juvenile hormone (methyl farnesoate) treated: 100 pM | 1 nM |
|---|---|---|
| Yeast 1 of Invention | 0.10 | 0.08 |
| Control yeast 1 | 0.01 | 0.00 |

As shown in Table 5, reporter gene expression is induced in the presence of methyl farnesoate, which is a juvenile hormone, in the Yeast 1 of Invention comprising the response element. In the control yeast 1, in contrast, substantially no reporter activity was detected.

[Test Example 2] Assay of Reporter Activity of Yeast Transformant to Juvenile Hormones In the same manner as in Test Example 1, the Yeasts 2, 3, 4, 5, 6, 7, 9, 10, 11, 12, 13, 14, 15, 16, 17, 18, 19, and 20 of Invention were subjected to assays of reporter activity to methyl farnesoate. The test was performed in accordance with Test Example 1, and reporter activity of the yeasts indicated above was compared with that of the control yeasts 2, 3, and 4. The results are shown in Table 6 and Table 7.

TABLE 6

| Tested yeast transformant | Amount of juvenile hormone (methyl farnesoate) treated | | | | |
|---|---|---|---|---|---|
| | 10 nM | 100 nM | 1 µM | 10 µM | 100 µM |
| Yeast 2 of Invention | 0.54 | 1.26 | 1.45 | 1.64 | 1.57 |
| Yeast 3 of Invention | 2.05 | 4.35 | 4.45 | 4.07 | 4.29 |
| Yeast 4 of Invention | 5.13 | 7.55 | 7.12 | 7.44 | 7.47 |
| Yeast 5 of Invention | 1.33 | 3.29 | 3.72 | 3.76 | 4.05 |
| Yeast 6 of Invention | 0.33 | 1.19 | 1.18 | 1.33 | 1.33 |
| Yeast 7 of Invention | 0.06 | 0.26 | 0.32 | 0.36 | 0.34 |
| Control yeast 2 | −0.29 | −0.27 | −0.34 | −0.21 | −0.14 |
| Control yeast 3 | −0.12 | −0.21 | −0.27 | −0.17 | −0.17 |
| Control yeast 4 | −0.84 | −1.49 | −1.82 | −1.05 | −2.06 |

TABLE 7

| Tested yeast transformant | Amount of juvenile hormone (methyl farnesoate) treated | |
|---|---|---|
| | 100 nM | 10 µM |
| Yeast 9 of Invention | 0.19 | 0.16 |
| Yeast 10 of Invention | 0.08 | 0.20 |
| Yeast 11 of Invention | 0.22 | 0.24 |
| Yeast 12 of Invention | 1.43 | 2.55 |
| Yeast 13 of Invention | — | 0.09 |
| Yeast 14 of Invention | — | 0.09 |
| Yeast 15 of Invention | 0.09 | 0.16 |
| Yeast 16 of Invention | 0.65 | 1.32 |
| Yeast 17 of Invention | 0.06 | 0.09 |
| Yeast 18 of Invention | 0.10 | — |
| Yeast 19 of Invention | 1.53 | 2.27 |
| Yeast 20 of Invention | 1.55 | 1.85 |

As shown in Table 6 and Table 7, it is apparent that potent expression of the reporter gene is induced in the presence of a juvenile hormone (methyl farnesoate) in the Yeasts 2, 3, 4, 5, 6, 7, 9, 10, 11, 12, 13, 14, 15, 16, 17, 18, 19, and 20 of Invention. In contrast, the increase of induction was negative in the control yeasts 2, 3, and 4 in any amount of treatment, and such control yeasts did not show any reporter activity. The results demonstrate that use of a nucleotide sequence comprising a total of 20 to 60 nucleotides including the nucleotide sequence shown in SEQ ID NO: 1 as a response element would enable evaluation of reporter activity to methyl farnesoate, which is a juvenile hormone, with high sensitivity.

[Test Example 3] Influence of Core Sequence on Reporter Activity of Yeast Transformant With the use of the control yeast 7 comprising a different nucleotide sequence of the C-box (CACGCG) in the response element, the control yeast 8 comprising a different nucleotide sequence of the E-box (CACGTG), and the control yeast 9 comprising different nucleotide sequences of the C-box and the E-box from the relevant nucleotide sequences of the Yeast 4 of Invention, the influence of a core sequence on reporter activity to methyl farnesoate was evaluated. The test was performed in accordance with Test Example 1. The results are shown in Table 8.

TABLE 8

| Tested yeast transformant | Amount of juvenile hormone (methyl farnesoate) treated | |
|---|---|---|
| | 100 nM | 10 µM |
| Yeast 4 of Invention | 0.42 | 0.51 |
| Control yeast 7 | −0.42 | −0.12 |
| Control yeast 8 | 0.00 | −0.02 |
| Control yeast 9 | −0.42 | −0.12 |

As shown in Table 8, high reporter activity to methyl farnesoate was induced in the Yeast 4 of Invention. In the control yeasts 7, 8, and 9 each comprising different nucleotide sequences in the C-box and/or the E-box, in contrast, reporter activity was lowered to a significant extent, compared to the Yeast 4 of Invention.

[Test Example 4] Assay of Reporter Activity of Yeast Transformant to Sex Hormones and Chemical Substances Suspected of Having Endocrine Disrupting Actions With the use of the Yeast 4 and the Yeast 8 of the present Invention, reporter activity to sex hormones; i.e., 17β-estradiol and testosterone, insect juvenile hormones; i.e., juvenile hormone III, and chemical substances suspected of having endocrine disrupting actions, such as 4-nonyl phenol, bisphenol A, 1,1,1-trichloro-2,2-bis(4-chlorophenyl)ethane (DDT), 2,2-bis(4-chlorophenyl)-1,1-dichloroethylene (DDE), and dieldrin, was assayed. The test was performed in accordance with Test Example 1. All the test substances were treated at 10 µM. For comparison, reporter activity to compounds was assayed using the control yeast 5 and the control yeast 6 comprising a known juvenile hormone receptor response element (i.e., the JH response element of *Drosophila melanogaster*) integrated therein. The results are shown in Table 9.

TABLE 9

| Tested yeast transformant | Increase in induction | | | | | | | |
|---|---|---|---|---|---|---|---|---|
| | 17β-estradiol | Testosterone | Juvenile hormone III | 4-nonyl phenol | Bisphenol A | DDT | DDE | Dieldrin |
| Yeast 4 of Invention | 1.97 | 1.78 | 6.20 | 2.16 | 1.14 | 0.65 | 2.15 | 3.85 |
| Yeast 8 of Invention | 1.01 | 0.98 | 1.45 | 1.81 | 0.52 | 0.37 | 1.23 | 0.89 |
| Control yeast 5 | −0.14 | −0.02 | 0.41 | 0.74 | −0.38 | −0.07 | −0.08 | 0.00 |
| Control yeast 6 | −0.29 | −0.22 | 0.58 | 3.05 | −0.23 | −0.24 | −0.19 | −0.02 |

Concentration (10 µM)

As shown in Table 9, reporter gene expression was induced in the Yeast 4 and the Yeast 8 of Invention, regardless of endocrine disrupting chemical types. Thus, the response element of the present invention was found to be responsive to all the tested endocrine disrupting chemicals. The Yeast 8 of Invention is a transformant having a transcription factor of *Drosophila melanogaster* (DmMET). The response element of the present invention was found to be responsive to, in addition to a transcription factor of *Crustacea*, a transcription factor of an insect; i.e., *Drosophila melanogaster*. In contrast, reporter gene expression was induced only in systems using juvenile hormone III and 4-nonyl phenol in the control yeast 5 and the control yeast 6 each having a juvenile hormone response element of *Drosophila melanogaster* (DmJHRR), and DmJHRR did not show responsiveness to other endocrine disrupting chemicals. The results demonstrate that reporter assays involving the use of the response element of the present invention enable detection of endocrine disrupting chemicals exerting various actions.

[Test Example 5] Assay of Reporter Activity to Antagonist Substance for Juvenile Hormone Receptors With the use of the yeast 4 of the present invention, antagonist activity of juvenile hormone receptors to endrin, aldrin, and dieldrin was evaluated at 10 μM. The test was performed in accordance with Test Example 1, except that the test was performed in the presence of 10 nM methyl farnesoate. The results are shown in Table 10.

TABLE 10

| | Increase in induction | | |
|---|---|---|---|
| Tested yeast transformant | Endrin | Aldrin | Dieldrin |
| Yeast 4 of Invention | −0.03 | −9.02 | −12.46 |

0: Group treated with 10 nM methyl farnesoate
Concentration (10 μM)

As shown in Table 10, the Yeast 4 of Invention was found to suppress an increase in the reporter activity caused by methyl farnesoate on all the tested substances. The results demonstrate that the use of a transformant comprising the response element of the present invention integrated thereinto enables detection of endocrine disrupting chemicals exerting antagonist activity.

[Test Example 6] Assay of Reporter Activity of Yeast Transformant to Active Ingredients of Conventional Agricultural Chemicals In accordance with Test Example 1, endocrine disrupting actions on active ingredients of conventional agricultural chemicals; i.e., mepanipyrim, benthiavalicarb isopropyl, pyribencarb, pyroxasulfone, and fenquinotrione, were assayed using the Yeast 4 of Invention. Active ingredients of conventional agricultural chemicals were tested at 100 μM. All the tested active ingredients of conventional agricultural chemicals are known to exert no endocrine disrupting actions. The results are shown in Table 11.

TABLE 11

| Tested yeast | Increase in induction | | | | |
|---|---|---|---|---|---|
| transformant | Mepanipyrim | Benthiavalicarb isopropyl | Pyribencarb | Pyroxasulfone | Fenquinotrione |
| Yeast 4 of Invention | −0.76 | −0.37 | −0.24 | −0.50 | −0.24 |

Concentration (100 μM)

As shown in Table 11, reporter gene expression was not induced in the transformant comprising the response element of the present invention on all the active ingredients of conventional agricultural chemicals at 100 μM. The results demonstrate that a transformant comprising a nucleic acid encoding a receptor for endocrine disrupting chemicals having transcription factor activity, the response element according to the present invention, and a reporter gene introduced thereinto enables selective detection of endocrine disrupting chemicals.

[Test Example 7] Influence of Peripheral and Linker Regions of Core Sequence on Reporter Activity of Yeast Transformant The influence of the core sequence on reporter activity to methyl farnesoate was evaluated using the Yeasts 21, 22, 23, and 24 of Invention comprising a nucleotide sequence derived from the nucleotide sequence shown in SEQ ID NO: 2 by substitution of 3 nucleotides outside the 5' terminus of the C-box (CACGCG) in the response element; the Yeasts 25, 26, 27, and 28 of Invention comprising a nucleotide sequence derived from the nucleotide sequence shown in SEQ ID NO: 2 by substitution of 3 nucleotides outside the 3' terminus of the E-box (CACGTG) in the response element; the Yeasts 29, 30, and 31 of Invention comprising a nucleotide sequence derived from the nucleotide sequence shown in SEQ ID NO: 2 by substitution of 3 nucleotides outside the 5' terminus of the C-box (CACGCG) and 3 nucleotides outside the 3' terminus of the E-box (CACGTG) in the response element; the Yeasts 32, 33, 34, and 35 of Invention each comprising a different nucleotide sequence in a region between the C-box and the E-box (a linker region); and the Yeasts 36, 37, and 38 of Invention comprising a nucleotide sequence derived from the nucleotide sequence shown in SEQ ID NO: 2 by substitution of 3 nucleotides outside the 5' terminus of the C-box (CACGCG), 3 nucleotides outside the 3' terminus of the E-box (CACGTG), and a region between the C-box and the E-box (a linker region). Methyl farnesoate was treated at 100 nM and 10 μM. The test was performed in accordance with Test Example 1. The results are shown in Table 12.

TABLE 12

| | Amount of juvenile hormone (methyl farnesoate) treated | |
|---|---|---|
| Tested yeast transformant | 100 nM | 10 μM |
| Yeast 21 of Invention | 0.20 | 0.19 |
| Yeast 22 of Invention | 0.10 | 0.20 |
| Yeast 23 of Invention | 0.49 | 1.09 |
| Yeast 24 of Invention | 0.93 | 1.66 |

TABLE 12-continued

| Tested yeast transformant | Amount of juvenile hormone (methyl farnesoate) treated | |
|---|---|---|
| | 100 nM | 10 μM |
| Yeast 25 of Invention | 0.06 | 0.15 |
| Yeast 26 of Invention | 0.35 | 0.38 |
| Yeast 27 of Invention | 0.03 | 0.64 |
| Yeast 28 of Invention | 1.87 | 2.51 |
| Yeast 29 of Invention | 0.07 | 0.07 |
| Yeast 30 of Invention | 0.16 | 0.07 |
| Yeast 31 of Invention | 0.09 | 0.23 |
| Yeast 32 of Invention | 0.11 | 0.31 |
| Yeast 33 of Invention | 0.42 | 0.22 |
| Yeast 34 of Invention | 0.66 | 2.15 |
| Yeast 35 of Invention | 1.44 | 1.05 |
| Yeast 36 of Invention | 0.06 | 1.38 |
| Yeast 37 of Invention | 0.17 | 0.13 |
| Yeast 38 of Invention | 0.09 | 0.04 |

As shown in Table 12, it is apparent that reporter gene expression is more potently induced in the presence of juvenile hormone (methyl farnesoate) in the Yeasts 21, 22, 23, 24, 25, 26, 27, 28, 29, 30, 31, 32, 33, 34, 35, 36, 37, and 38 of Invention. The results demonstrate that a nucleotide sequence consisting of a total of 20 to 60 nucleotides would enable evaluation of reporter activity to methyl farnesoate, which is a juvenile hormone, with high sensitivity, even if 4 nucleotides in a region (a linker region) between the C-box (CACGCG) and the E-box (CACGCG) are kmkk (wherein k indicates G or t; and m indicates A or C) or, for example, TATT other than GCGG. Even if a nucleotide sequence in the vicinity of the nucleotide sequence shown in SEQ ID NO: 1 is different from the nucleotide sequence shown in SEQ ID NO: 2, in addition, reporter activity to juvenile hormone-like substances can also be evaluated with high sensitivity.

The invention claimed is:

1. A transformed host cell comprising a nucleic acid sequence wherein the nucleic acid sequence is selected from the group consisting of SEQ ID NOs: 2, 5, 8, 34, 37, 40, 43, 46, 49, and 52.

2. The transformed host cell according to claim 1, wherein the nucleic acid is designated as a unit and a plurality of units of the nucleic acids are bound to each other.

3. The transformed host cell according to claim 1, wherein the nucleic acid is double stranded and further comprises a reporter gene on the 3' terminal side of a sense strand of the nucleic acid.

4. The transformed host cell according to claim 1, which comprises a nucleic acid encoding a receptor for endocrine disrupting chemicals, wherein the receptor interacts with the nucleic acid introduced thereinto.

5. The transformed host cell according to claim 4, wherein the receptor for endocrine disrupting chemicals is a juvenile hormone receptor of arthropods.

6. The transformed host cell according to claim 5, wherein the juvenile hormone receptor of arthropods is a juvenile hormone receptor of *Crustacea* or an insect.

7. The transformed host cell according to claim 6, wherein the juvenile hormone receptor of *Crustacea* is a juvenile hormone receptor of daphnid.

8. The transformed host cell according to claim 7, wherein the juvenile hormone receptor of daphnid is a protein (a) or (b):

(a) a protein consisting of the amino acid sequence shown in SEQ ID NO: 12; or (b) a protein consisting of an amino acid sequence having 70% or higher identity to the amino acid sequence shown in SEQ ID NO: 12 and having activity of a transcription factor for a juvenile hormone receptor.

9. The transformed host cell according to claim 1, which further comprises a nucleic acid encoding a transcription-coupling factor introduced thereinto.

10. The transformed host cell according to claim 1, wherein the host is a yeast.

* * * * *